(12) United States Patent
Lee et al.

(10) Patent No.: US 9,987,275 B2
(45) Date of Patent: Jun. 5, 2018

(54) TARGETING PARP1 FOR TREATMENT OF TSC AND CANCERS

(71) Applicant: THE BRIGHAM AND WOMEN'S HOSPITAL, INC., Boston, MA (US)

(72) Inventors: Po-Shun Lee, Boston, MA (US); Jane Yu, Boston, MA (US); Yang Sun, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days. days.

(21) Appl. No.: 15/305,883

(22) PCT Filed: Apr. 23, 2015

(86) PCT No.: PCT/US2015/027264
§ 371 (c)(1),
(2) Date: Oct. 21, 2016

(87) PCT Pub. No.: WO2015/164586
PCT Pub. Date: Oct. 29, 2015

(65) Prior Publication Data
US 2017/0049771 A1 Feb. 23, 2017

Related U.S. Application Data

(60) Provisional application No. 61/983,078, filed on Apr. 23, 2014.

(51) Int. Cl.
*A61K 38/00* (2006.01)
*C12N 15/113* (2010.01)
*A61K 31/4725* (2006.01)
*A61K 31/502* (2006.01)
*A61K 31/517* (2006.01)
*A61K 31/713* (2006.01)
*A61K 31/4985* (2006.01)

(52) U.S. Cl.
CPC ........ *A61K 31/502* (2013.01); *A61K 31/4725* (2013.01); *A61K 31/4985* (2013.01); *A61K 31/517* (2013.01); *A61K 31/713* (2013.01); *A61K 38/00* (2013.01); *C12N 15/1137* (2013.01); *C12Y 204/0203* (2013.01); *C12N 15/113* (2013.01); *C12N 2310/14* (2013.01)

(58) Field of Classification Search
None
See application file for complete search history.

(56) References Cited

FOREIGN PATENT DOCUMENTS

| WO | 2013/052006 A1 | 4/2013 |
| WO | 2013/074583 A1 | 5/2013 |

OTHER PUBLICATIONS

Kummar et al (BMC Medicine 2012, 10:25).*
Xie et al (F1000Research 2016, 5(F1000 Faculty Rev):2078).*
https://clinicaltrials.gov/ct2/show/NCT01286987, retrieved from the web on Jun. 2, 2017.*
Goldberg et al (Proc Nat Acad Sci USA 108(2): 745-750, 2011).*
Dressler (J Cancer Res Clin Oncol (2013) 139:1349-1355).*
Shimobayashi et al (Cell Res. 6:7-20, 2016).*
Kummar et al (BMC Medicine 2012, 10:25) Additional Table 1.*
Kummar et al (BMC Medicine 2012, 10:25) Additional Table 2.*
Finlay et al., "Platelet-derived growth factor-induced p42/44 mitogen-activated protein kinase activation and cellular growth is mediated by reactive oxygen species in the absence of TSC2/tuberin", Cancer Res, 65(23):10881-90 (2005).
Javle et al., "The role of PARP in DNA repair and its therapeutic exploitation", Br J Cancer, 105(8):1114-22 (2011).
Karbowniczek et al., "Regulation of B-Raf kinase activity by tuberin and Rheb is mammalian target of rapamycin (mTOR)-independent", J Biol Chem, 279(29):29930-7 (2004).
Karbowniczek et al., "Rheb inhibits C-raf activity and B-raf/C-raf heterodimerization", J Biol Chem, 281 (35):25447-56 (2006).
Landi et al., "Gene expression signature of cigarette smoking and its role in lung adenocarcinoma development and survival", PLoS One, 3(2):e1651 (2008).
Lee et al., "Rapamycin-insensitive up-regulation of MMP2 and other genes in tuberous sclerosis complex 2-deficient lymphangioleiomyomatosis-like cells", Am J Respir Cell Mol Biol, 42(2):227-34 (2010).
Lu et al., "Identification of a novel biomarker, SEMA5A, for non-small cell lung carcinoma in nonsmoking women", Cancer Epidemiol Biomarkers Prev, 19(10):2590-7 (2010).
Pena-Llopis et al., "Regulation of TFEB and V-ATPases by mTORC1", EMBO J, 30(16):3242-58 (2011).
Sousa et al., "PARPs and the DNA damage response", Carcinogenesis, 33(8):1433-40 (2012).
Zhou et al., "Poly(ADP-ribose) polymerase-1 regulates the mechanism of irradiation-induced CNE-2 human nasopharyngeal carcinoma cell autophagy and inhibition of autophagy contributes to the radiation sensitization of CNE-2 cells", Oncol Rep, 29(6):2498-506 (2013).
Clovis Oncology Inc., "A Study of Rucaparib in Patients With Platinum-Sensitive, Relapsed, High-Grade Epithelial Ovarian, Fallopian Tube, or Primary Peritoneal Cancer (ARIEL2)", ClinicalTrials.gov: Archive: NCT01891344 (2013). Retrieved from the Internet (https://clinicaltrials.gov/archive/NCT01891344/2013_12_10).
Pinton et al., "PARP1 inhibition affects pleural mesothelioma cell viability and uncouples AKT/mTOR axis via SIRT1", J Cell Mol Med, 17(2):233-41 (2013).
Sun et al., "Rapamycin-resistant poly (ADP-ribose) polymerase-1 overexpression is a potential therapeutic target in lymphangioleiomyomatosis", Am J Respir Cell Mol Biol, 51(6):738-49 (2014).

* cited by examiner

*Primary Examiner* — Richard A Schnizer
(74) *Attorney, Agent, or Firm* — Nixon Peabody LLP; Mark J. FitzGerald; Srividya Subramanian

(57) ABSTRACT

The present invention relates to methods of treating a condition associated with mTORC1 hyperactivation or TSC2-deficient cancer, the method comprising administering to a subject having the cancer a pharmaceutically-effective amount of a poly(ADP-ribose) polymerase 1 (PARP1) inhibitor. In some embodiments, the condition associated with mTORC1 hyperactivation is tuberous sclerosis complex (TSC). In some embodiments, the condition associated with mTORC1 hyperactivation is lymphangioleiomyomatosis (LAM). In some embodiments, the condition associated with mTORC1 hyperactivation is TSC2-deficient cancer.

8 Claims, 9 Drawing Sheets

A

B

C

TARGETING PARP1 FOR TREATMENT OF TSC AND CANCERS

CROSS-REFERENCE TO RELATED APPLICATIONS

This application is a 35 U.S.C. § 371 National Phase Entry Application of International Application No. PCT/US2015/027264 filed Apr. 23, 2015, which designates the U.S., and which claims benefit under 35 U.S.C. § 119(e) of U.S. Provisional Application No. 61/983,078 filed Apr. 23, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 11, 2015, is named 043214-081561-PCT_SL.txt and is 5,284 bytes in size.

GOVERNMENT SUPPORT

This invention was made with government support under grant HL098216 awarded by National Heart, Lung, and Blood Institute. The government has certain rights in the invention.

TECHNICAL FIELD

The present invention relates generally to methods of treatment for tuberous sclerosis complex (TSC), lymphangioleiomyomatosis (LAM), and/or other cancers.

BACKGROUND

Lymphangioleiomyomatosis (LAM) is a progressive cystic lung disease that predominantly affects women of childbearing age. LAM is characterized by proliferation of abnormal smooth muscle-like cells in nodules in the lung parenchyma and other sites, and by cystic changes with lung tissue destruction. LAM occurs in 30-40% of women with tuberous sclerosis complex (TSC). LAM can also occur as a sporadic disease in women who do not have generalized features of TSC. TSC is due to germline mutations in either TSC1 or TSC2, and similar inactivating somatic mutations are found in LAM cells from sporadic LAM patients.

About 60% of women with the sporadic form of LAM also have renal angiomyolipomas. The presence of TSC2 mutations in LAM cells and renal angiomyolipoma cells from women with sporadic LAM, but not in normal tissues, has led to the model that LAM cells spread to the lungs via a metastatic mechanism. Genetic analyses of recurrent LAM after lung transplantation also support the metastatic model for LAM pathogenesis. The only treatment for end-stage LAM and respiratory failure is lung transplantation, with its intrinsic limitations. Furthermore LAM can recur in the transplanted lungs.

LAM cells typically have inactivating TSC2 mutations and mTORC1 activation. However, clinical response to mTORC1 inhibitors has been limited. Accordingly, there is an unmet need for new treatments for LAM.

SUMMARY

The technology described herein is based, inter alia, on the discovery that PARP1 is overexpressed in TSC2-deficient cells derived from LAM patients, and that PARP1 expression appears to be insensitive to mTORC1 inhibitors such as rapamycin or Torin1. PARP1 can be targeted for the treatment of LAM, or other conditions associated with mTORC1 hyperactivation, or TSC2-deficient cancers. Without wishing to be bound by theory, because TSC2 regulates PARP1 expression, PARP1 expression can indicate abnormal TSC2 function. In addition, because TSC2 is direct upstream of mTORC1, abnormal TSC2 function (e.g., TSC2 deficiency) can cause mTORC1 hyperactivation. Therefore PARP1 expression is correlated with mTORC1 hyperactivation.

Accordingly, in one aspect, the technology described herein relates to a method of treating a condition associated with mTORC1 hyperactivation, the method comprising administering to a subject having the condition a pharmaceutically-effective amount of a poly(ADP-ribose) polymerase 1 (PARP1) inhibitor. In some embodiments, the condition associated with mTORC1 hyperactivation is selected from the group consisting of tuberous sclerosis complex (TSC), lymphangioleiomyomatosis (LAM), and TSC2-deficient cancer. In some embodiments, the condition associated with mTORC1 hyperactivation is tuberous sclerosis complex (TSC). In some embodiments, the condition associated with mTORC1 hyperactivation is lymphangioleiomyomatosis (LAM). In some embodiments, the condition associated with mTORC1 hyperactivation is TSC2-deficiency.

In another aspect, the technology described herein relates to a method of treating TSC2-deficient cancer, the method comprising administering to a subject having the cancer a pharmaceutically-effective amount of a poly(ADP-ribose) polymerase 1 (PARP1) inhibitor.

In some embodiments of any one of the above aspects, the PARP1 inhibitor is selected from the group consisting of a small molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof.

In some embodiments of any one of the above aspects, the PARP1 inhibitor is selected from the group consisting of 8-hydroxy-2-methylquinazoline-4-one, 3,4-dihydro-5[4-(1-piperindinyl)butoxy]-1(2H)-isoquinoline, 3-aminobenzamide, olaparib, iniparib, rucaparib, veliparib, talazoparib, niraparib, CEP-9722, BGB-290, AG-14361, A-966492 and BMN673.

In some embodiments of any one of the above aspects, the PARP1 inhibitor is a small interfering RNA (siRNA).

In some embodiments of any one of the above aspects, the subject is a mammal.

In some embodiments of any one of the above aspects, the subject is a human.

In some embodiments of any one of the above aspects, the administering is systemic.

In some embodiments of any one of the above aspects, the administering is local.

BRIEF DESCRIPTION OF THE DRAWINGS

(FIG. 1A) Cellular levels of ROS in TSC2-null cells and TSC2-addback cells were measured. (FIG. 1B) Representative immunofluorescent staining images of phospho-γH2A.X in patient-derived cells. Scale bars, 30 μM. ** P<0.01, Student's t-test.

(FIG. 2A) Global gene expression assay was performed using RNA isolated from patient-associated angiomyolipoma-derived TSC2-deficient cells (TSC2−), TSC2-addback cells (TSC2+), and TSC2-deficient cells treated with rapamycin for 24 hr (TSC2-R). The heatmap shows differentially expressed PARP genes. (FIG. 2B) Transcript levels of PARP family members were compared between TSC2-deficient (TSC2−) and TSC2-addback (TSC2+) cells, or rapamycin- and vehicle-treated TSC2-deficient cells (Rapa TSC2−). (FIG. 2C) Comparison of the differentially expressed PARP genes in four independent expression arrays including one data set of LAM patient-derived and three $Tsc2^{-/-}$ and $Tsc2^{+/+}$ MEFs (MEF-1, -2 and -3). (FIG. 2D) Comparison of the differentially expressed PARP family member in four independent expression array. ** P<0.01, *P<0.05, Student's t-test.

(FIG. 3A) The relative level of PARP1 in the microarray of patient-associated angiomyolipoma-derived cells compared with cells treated with rapamycin or TSC2 addback cells. (FIG. 3B) The transcript levels of PARP1 in LAM patient-derived cells treated with rapamycin or vehicle. (FIGS. 3C-3D) TSC2-deficient or TSC2-addback cells (LAM patient-derived or Rat-derived cells) were treated with 20 nM rapamycin for 24 hr. Immunoblots of PARP1, phospho-S6 and S6 were shown. (FIG. 3E) Cells were treated with siRNAs to various mTOR components, and lysates were subjected to immunoblotting. Knockdown of either mTOR or raptor (Rap) reduced phospho-S6 (S240/244) levels compared to cells treated with nonsense control (NC) siRNA. (FIG. 3F) TSC2-deficient patient-derived cells were treated with vehicle (Con), rapamycin (Rapa, 20 nM), or Torin1 (0.05, 0.25, 0.5 and 1 μM) for 4 hr. Immunoblots of PARP1 and phospho-S6 were shown. Duplicate lanes were loaded. Rapamycin (rapa) at 20 nM suppressed mTORC1 as reflected by lower phospho-S6 levels while PARP inhibitors DPQ and NU1025 had no effect on phospho-S6 levels. ** P<0.01, *P<0.05, Student's t-test.

(FIG. 4A) Immunoblots of PARP1 and phospho-S6 in xenograft tumors from Tsc2-deficient rat uterine-derived cells (TSC2−) and TSC2-addback cells (TSC2+). (FIG. 4B) $Tsc2^{+/-}$ mice were treated with rapamycin (6 mg/kg/day, i.p.) or vehicle control for one week. Representative microscopic images of immunohistochemistry of PARP1 on renal tumor sections. Kidney cystadenomas stained heavily (dark brown) for PARP1, especially within the nuclei (pointed by arrows). Normal kidney tubules were also noted tumors stained lightly for PARP1 while glomeruli stained negative. (FIG. 4C) Immunoblots of PARP1 and phospho-S6 in kidney cystadenomas (T) and adjacent normal kidney (N) from $Tsc2^{+/-}$ mice. Tubulin was used as a loading control.

(FIG. 5A) The public expression array data of LAM lung cells, lung tumors and normal lungs were analyzed. The transcript levels of PARP1 were shown. (FIG. 5B) Immunoblots show the protein levels of PARP1 and phospho-S6 in LAM lung and normal lung tissues. (FIG. 5C) Immunohistochemical staining of smooth muscle actin and PARP1 in pulmonary LAM nodules (LAM-1 and LAM-2). (FIG. 5D) LAM lung tissue sections stained for SM α-actin and PARP1. ** P<0.01, Student's t-test.

(FIG. 6A) Immunoblots of PARP1, phospho-Akt and phospho-S6 in TSC2-deficient patient-derived cells treated with DPQ or NU1025. Patient-derived TSC2-deficient (TSC2−) (FIG. 6B) Immunoblots of PARP1, PAR and β-actin in TSC2-deficient patient-derived cells. (FIG. 6C) Cell viability of patient-derived cells including TSC2-deficient and TSC2 addback cells treated with PARP1 inhibitors (DPQ 1-30 μM Olaparib 1-30 μM) with or without combination of rapamycin (20 nM). Cell viability was measured using MTT assay. (FIG. 6D) Cell proliferation of patient-derived cells including TSC2-deficient and TSC2 addback cells treated with PARP1 inhibitors (DPQ 1-30 μM Olaparib 1-30 μM) with or without combination of rapamycin (20 nM). Cell proliferation was measured using crystal violet assay. ** P<0.01, *P<0.05, Student's t-test.

(FIG. 7A) Cell death of patient-derived cells including TSC2-deficient and TSC2-addback cells treated with PARP1 inhibitors (DPQ 1-30 μM Olaparib 1-30 μM) with or without combination of rapamycin (20 nM). Cell death was measure using PI exclusion assay. (FIG. 7B) Cell death of patient-derived cells including TSC2-deficient and TSC2 addback cells treated with PARP1 inhibitors (DPQ 1-30 μM Olaparib 1-30 μM) with or without combination of $H_2O_2$ (0.5 mM). Cell death was measure using PI exclusion assay. (FIG. 7C) Patient-derived TSC2-deficient and TSC2-addback cells were treated with NU1025 (10 μM), DPQ (10 μM) for 24 hr, and then treated with $H_2O_2$ (0.5 mM) for 1 hr. Cell death was analyzed for PI and Annexin V staining by flow cytometry. Percentage of PI positive, Annexin V positive or double positive cells was summarized. ** P<0.01, *P<0.05, Student's t-test. (FIG. 7D) Model demonstrating the role of PARP1 in LAM pathogenesis. Without wishing to be bound by theory, it is believed that loss of TSC2 results in hyperactivation of mTOR, increased ROS production, and uncontrolled cell proliferation. Rapamycin inhibits mTOR activity and suppresses cell proliferation. ROS causes DNA damage in TSC2-deficient cells, leading to PARP1 expression. PARP1 repairs DNA damage and enhances cell survival under oxidative stress. Inhibition of PARP1 leads to death of LAM patient-derived cells, supporting the use of this approach for therapy.

DETAILED DESCRIPTION

Figures 1A, 1B:
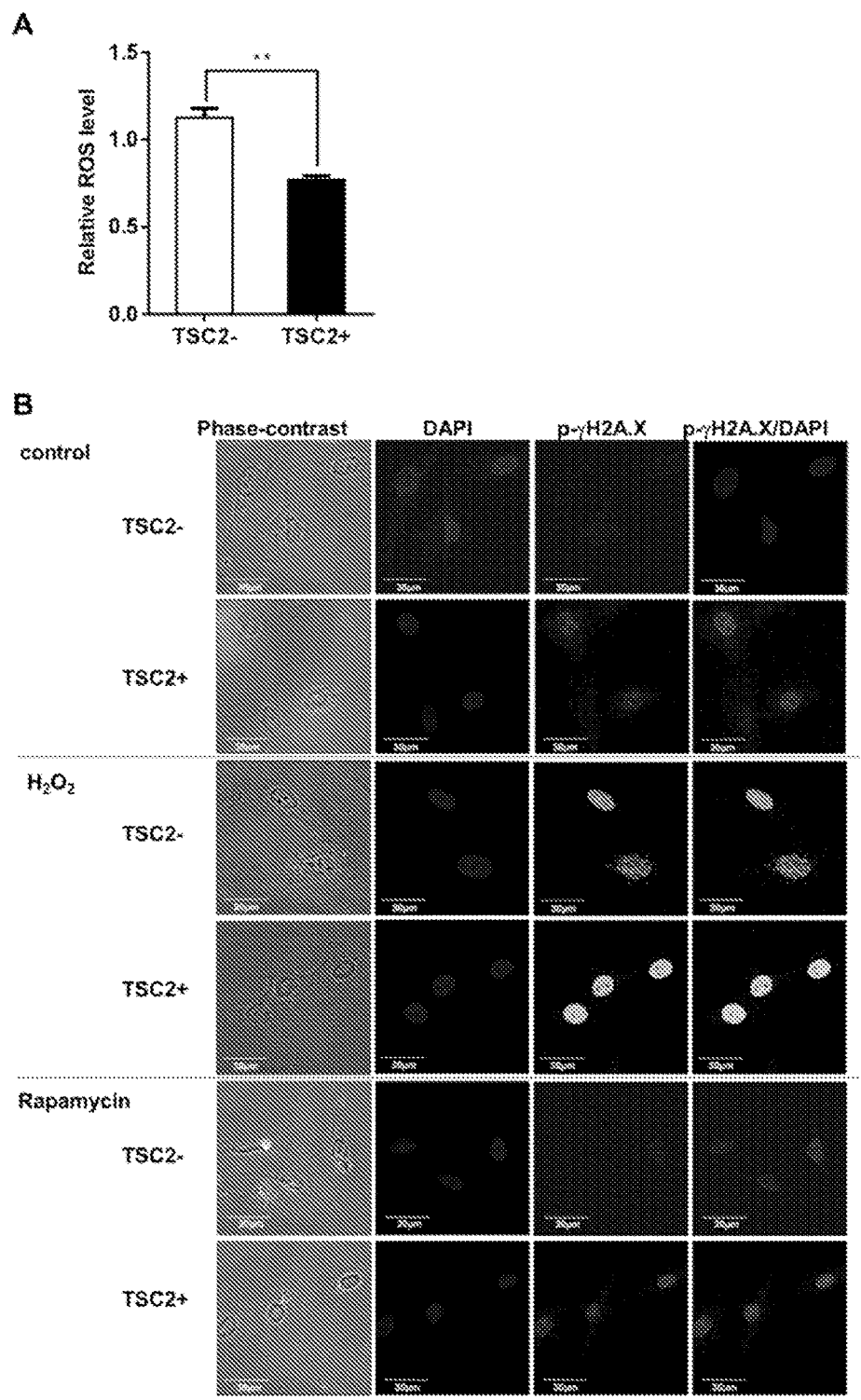
FIGS. 1A-1B describe experimental data demonstrating that tuberin attenuates ROS production and promotes DNA damage. Patient-derived TSC2-deficient (TSC2−) and TSC2-addback (TSC2+) cells were treated with vehicle, 20 nM rapamycin or 0.5 mM $H_2O_2$.

PARP1 (Poly [ADP-ribose] polymerase 1), a member of the PARP family of proteins, is a large abundant nuclear protein activated by DNA damage, which plays a role in chromosomal repair and stability. It has been discovered and described herein that the PARP1 level is increased in TSC2-deficient cells derived from LAM patients relative to TSC2-addback cells, and that inhibition of PARP1 suppresses growth and promotes apoptosis of TSC2-deficient cells, making PARP1 a therapeutic target for disorders involving TSC2 deficiency. These TSC2-deficient cells typically have inactivating TSC2 mutations and mTORC1 activation. It has been further discovered that PARP1 expression in these TSC2-deficient cells is insensitive to mTORC1 inhibitors. Therefore, PARP1 can be targeted independently from mTORC1.

Some aspects and embodiments of the technology described herein relate to methods of treatment for TSC2-deficient cancers by administering a therapeutically-effective amount of a PARP1 inhibitor.

Additionally, some aspects and embodiments of the technology described herein relate to methods of treatment for conditions associated with mTORC1 hyperactivation by administering a therapeutically-effective amount of a PARP1 inhibitor. In some embodiments, the condition associated with mTORC1 hyperactivation is selected from the group consisting of tuberous sclerosis complex (TSC), lymphangioleiomyomatosis (LAM), and cancer (e.g., TSC2-deficient cancer).

TSC is a genetic disorder that causes non-malignant tumors to form in many different organs, primarily in the brain, eyes, heart, kidney, skin and lungs. TSC can be diagnosed by identifying a combination of signs including, but not limited to, facial angiofibromas or forehead plaque, nontraumatic ungual or periungual fibroma, hypomelanotic macules, Shagreen patch, cortical tuber, subependymal nodule, subependymal giant cell astrocytoma, multiple retinal nodular hamartomas, cardiac rhabdomyoma, lymphangioleiomyomatosis, renal angiomyolipoma, multiple randomly distributed pits in dental enamel, hamartomatous rectal polyps, bone cysts, cerebral white-matter "migration tracts", gingival fibromas, nonrenal hamartoma, retinal achromic patch, "confetti" skin lesions, multiple renal cysts, and multifocal micronodular pneumocyte hyperplasia.

In patients with typical cystic changes on high resolution CT scanning, serum levels of vascular endothelial growth factor-D greater than 800 pg/mL are considered to be diagnostic for LAM. A lung biopsy can be used to make a diagnosis for LAM. Serum VEGF-D can also be a useful biomarker for diagnosis of LAM. Symptoms of LAM can include, but are not limited to, shortness of breath on exertion, cough, hemoptysis, recurrent pneumothorax, chylous pleural effusion and chylous ascites.

In some embodiments, the PARP1 inhibitor is a small or large organic or inorganic molecule. As used herein, the term "small molecule" refers to natural or synthetic molecules having a molecular weight less than about 10,000 grams per mole, organic or inorganic compounds having a molecular weight less than about 5,000 grams per mole, less than about 1,000 grams per mole, or less than about 500 grams per mole.

In some embodiments, the PARP1 inhibitor can be an antibody molecule or an antigen-binding fragment thereof. Suitable antibodies include, but are not limited to, polyclonal, monoclonal, chimeric, humanized, recombinant, single chain, Fab, Fab', Fsc, Fv, and F(ab')2 fragments, and an Fab expression library. In some embodiments, neutralizing antibodies can be used as inhibitors of PARP1. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

The PARP1 polypeptide, or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues.

Useful monoclonal antibodies and fragments can be derived from any species (including humans) or can be formed as chimeric proteins which employ sequences from more than one species. Human monoclonal antibodies or "humanized" murine antibody can also be used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction in the likelihood of adverse immune reactions in a manner similar to that disclosed in European Patent Application No. 0,411,893 A2. Thus, murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, provides one option for a smaller engineered antigen-binding construct. Techniques have been developed to display scFv molecules on the surface of filamentous phage that contain the gene for the scFv. scFv molecules with a broad range of antigenic-specificities can be present in a single large pool of scFv-phage as a library.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

PARP1 antibodies are commercially available from vendors such as Santa Cruz Biotech (Dallas, Tex.), Cell Signaling Technology (Danvers, Mass.), and Abcam (Cambridge, UK).

In some embodiments, the PARP1 inhibitor is a nucleic acid or a nucleic acid analog or derivative thereof, also referred to as a nucleic acid agent herein. In the context of this disclosure, the term "nucleic acid" refers to a polymer or oligomer of nucleotide or nucleoside monomers consisting of naturally occurring bases, sugars and inter-sugar linkages. The term "nucleic acid" or "oligonucleotide" or "polynucleotide" are used interchangeably herein and can mean at least two nucleotides covalently linked together. As will be appreciated by those skilled in the art, the depiction of a single strand also defines the sequence of the complementary strand. Thus, a nucleic acid also encompasses the complementary strand of a depicted single strand. As will also be appreciated by those skilled in the art, many variants of a nucleic acid can be used for the same purpose as a given nucleic acid. Thus, a nucleic acid also encompasses substantially identical nucleic acids and complements thereof.

Without limitation, the nucleic acid agent can be single-stranded or double-stranded. A single-stranded nucleic acid agent can have double-stranded regions and a double-stranded nucleic acid agent can have single-stranded regions. The nucleic acid can be of any desired length. In particular embodiments, nucleic acid can range from about 10 to 100 nucleotides in length. In various related embodiments, nucleic acid agents, single-stranded, double-stranded, and triple-stranded, can range in length from about 10 to about 50 nucleotides, from about 20 to about 50 nucleotides, from about 15 to about 30 nucleotides, from about 20 to about 30 nucleotides in length. In some embodiments, nucleic acid agent is from about 9 to about 39 nucleotides in length. In some other embodiments, nucleic acid agent is at least 30 nucleotides in length.

The nucleic acid agent can comprise any nucleic acid or oligonucleotide modification described herein and below. In certain instances, it can be desirable to modify one or both strands of a double-stranded nucleic acid agent. In some cases, the two strands will include different modifications. In other instances, multiple different modifications can be included on each of the strands. The various modifications on a given strand can differ from each other, and can also differ from the various modifications on other strands. For example, one strand can have a modification, and a different strand can have a different modification. In other cases, one strand can have two or more different modifications, and the another strand can include a modification that differs from the at least two modifications on the first strand.

Single-stranded and double-stranded nucleic acid agents that are effective in inducing RNA interference are referred to as siRNA, RNAi agent, iRNA agent, or RNAi inhibitor herein. As used herein, the term "iRNA agent" refers to a nucleic acid agent which can mediate the targeted cleavage of an RNA transcript via an RNA-induced silencing complex (RISC) pathway.

As used herein, "target sequence" refers to a contiguous portion of the nucleotide sequence of an mRNA molecule formed during the transcription of a PARP1 gene, including messenger (mRNA) that is a product of RNA processing of a primary transcription product. The target portion of the sequence will be at least long enough to serve as a substrate for iRNA-directed cleavage or binding of antisense RNA/oligonucleotide at or near that portion. For example, the target sequence will generally be from 9-36 nucleotides in length, e.g., 15-30 nucleotides in length, including all subranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Further, the target sequence can start at any desired nucleotide position of the given target RNA.

Human PARP1 mRNA sequences are known (NCBI Reference Sequence: NM_001618.3). In some embodiments, the nucleic acid agent comprises a nucleotide substantially complementary to 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides contiguous nucleotides of one of the above-noted PARP1 mRNA sequences.

In some embodiments, the PARP1 inhibitor is an antisense oligonucleotide. One of skill in the art is well aware that single-stranded oligonucleotides can hybridize to a complementary target sequence and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H and thus preventing translation of target RNA.

Alternatively, or in addition to, the single-stranded oligonucleotide can modulate the expression of a target sequence via RISC mediated cleavage of the target sequence, i.e., the single-stranded oligonucleotide acts as a single-stranded RNAi agent. A "single-stranded RNAi agent" as used herein, is an RNAi agent which is made up of a single molecule. A single-stranded RNAi agent can include a duplexed region, formed by intra-strand pairing, e.g., it can be, or include, a hairpin or pan-handle structure.

In some embodiments, the PARP1 inhibitor is a microRNA. MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S. NAR, 2004, 32, Database Issue, D109-D111; and also on the worldwide web at http://microrna.dot.sanger.dot.ac.dot.uk/sequences/.

In general, any method of delivering a nucleic acid molecule can be adapted for use with the nucleic acid agents described herein (see e.g., Akhtar S, and Julian R L., 1992, Trends Cell. Biol. 2 (5):139-144 and WO94/02595, which are incorporated by reference in their entireties). However, there are three factors that are important to consider in order to successfully deliver a nucleic acid agent in vivo: (a) biological stability of the delivered molecule, (2) preventing non-specific effects, and (3) accumulation of the delivered molecule in the target tissue. The non-specific effects of a nucleic acid agent can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that can degrade the agent, and permits a lower total dose of the agent to be administered. Several studies have shown successful knockdown of gene products when an iRNA agent is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering a nucleic acid agent systemically for the treatment of a disease, the nucleic acid agent can be modified or alternatively delivered using a drug delivery system; both methods act to prevent the rapid degradation of the nucleic acid agent by endo- and exo-nucleases in vivo. In an alternative embodiment, the nucleic acid agent can be delivered using drug delivery systems such as a nanoparticle, a dendrimer, a polymer, liposomes, or a cationic delivery system. Positively charged cationic delivery systems facilitate binding of a nucleic acid molecule (negatively charged) and also enhance interactions at the negatively charged cell membrane to permit efficient uptake of the nucleic acid agent by the cell. Cationic lipids, dendrimers, or polymers can either be bound to a nucleic acid agent, or induced to form a vesicle or micelle (see e.g., Kim S H., et al (2008) Journal of Controlled Release 129 (2): 107-116) that encases a nucleic acid agent. The formation of vesicles or micelles further prevents degradation of the nucleic acid agent when administered systemically. Methods for making and administering cationic-nucleic acid complexes are well within the abilities of one skilled in the art (see e.g., Sorensen, D R., et al (2003) J. Mol. Biol. 327: 761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of nucleic acids and cyclodextrins can be found in U.S. Pat. No. 7,427,605, which is herein incorporated by reference in its entirety.

In some embodiments, the PARP1 inhibitor can also be a peptide, a peptidomimetic, a protein, a monosaccharide, a disaccharide, a trisaccharide, an oligosaccharide, a polysaccharide, a lipid, a glycosaminoglycan, an extract made from a biological material, or any combinations thereof.

In some embodiments, the PARP1 inhibitor is 8-hydroxy-2-methylquinazoline-4-one (also called NU1025), 3,4-dihydro-5[4-(1-piperindinyl)butoxy]-1(2H)-isoquinoline (also called DPQ), 3-aminobenzamide, olaparib, iniparib, rucaparib, veliparib, talazoparib, niraparib, CEP-9722, BGB-290, AG-14361, A-966492, BMN673, or a combination thereof.

In some embodiments, the PARP1 inhibitor described herein can be administered in the form of a pharmaceutical composition comprising the PARP1 inhibitor, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a PARP1 inhibitor as described herein.

The pharmaceutical compositions useful in the methods described herein can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally the compounds described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments, the pharmaceutical composition comprising a PARP1 inhibitor as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of a PARP1 inhibitor as disclosed herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a PARP1 inhibitor as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the PARP1 inhibitor can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, a PARP1 inhibitor as described herein can be administered in a liposome formulation. As used herein, "lipid vesicle" or "liposome" refers to vesicles surrounded by a bilayer formed of lipid components usually including lipids optionally in combination with non-lipidic components. The interior of a vesicle is generally aqueous. One major type of liposomal composition not generally found in nature includes phospholipids other than naturally-derived phosphatidylcholine. Neutral lipid vesicle compositions, for example, can be formed from dimyristoyl phosphatidylcholine (DMPC) or dipalmitoyl phosphatidylcholine (DPPC). Anionic lipid vesicle compositions generally are formed from dimyristoyl phosphatidylglycerol. Another type of liposomal composition is formed from phosphatidylcholine (PC) such as, for example, soybean PC, and egg PC. Another type is formed from mixtures of phospholipid and/or phosphatidylcholine and/or cholesterol. Lipids for lipid vesicle or liposome formation are known in the art or described herein below. Liposomes are formed by the self-assembly of phospholipid molecules in an aqueous environment. The amphipathic phospholipid molecules form a closed bilayer sphere in an attempt to shield their hydrophilic groups from the aqueous environment, while still maintaining contact with the aqueous phase via the hydrophilic head group. The resulting closed sphere can encapsulate aqueous soluble drugs or agents within the bilayer membrane. Non-limiting examples of liposome compositions include those described U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556 each of which is incorporated herein by reference in its entirety.

In some embodiments, a PARP1 inhibitor as described herein can be administered in an oral formulation. Pharmaceutical compositions comprising PARP1 inhibitors of the present invention can also be formulated into oral dosage forms such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms are prepared by combining the pharmaceutically acceptable salt of the disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents. Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary. For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105

(available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

The excipient, binder, or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The term "effective amount" as used herein refers to the amount of a therapy needed to alleviate at least one or more symptoms of the disease or disorder, and relates to a sufficient amount of pharmacological composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount." However, for any given case, an appropriate "effective amount" can be determined by one of ordinary skill in the art using only routine experimentation.

In some embodiments, an effective amount of a PARP1 inhibitor can be an amount which causes the level of PARP1 expression to decrease.

In some embodiments, an effective amount of a PARP1 inhibitor can be an amount which causes nodule or tumor size to decrease or, at least, to increase at a lower rate than it would be expected to increase in a subject not receiving a composition as described herein.

In some embodiments, an effective amount of a PARP1 inhibitor can be an amount which reverses, slows down or stops the progression of TSC, LAM, or cancer such as TSC2-deficient cancer.

The dosage can be determined by one of skill in the art and can also be adjusted by the individual physician in the event of any complication. Typically, the dosage of a composition comprising a PARP1 inhibitor disclosed herein can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, the dosage of a composition comprising a PARP1 inhibitor disclosed herein can be administered in a dose of from about 20 $mg/m^2$ to about 5,000 $mg/m^2$ body surface area. For example, the dose can be from about 20 $mg/m^2$ to about 200 $mg/m^2$ body surface area; the dose can be from about 150 $mg/m^2$ to about 500 $mg/m^2$ body surface area; the dose can be from about 400 $mg/m^2$ to about 1000 mg/m² body surface area; the dose can be from about 900 mg/m² to about 5,000 mg/m² body surface area; the dose can be from about 200 mg/m² to about 1,000 mg/m² body surface area; or the dose can be from about 500 mg/m² to about 600 mg/m² body surface area.

In certain embodiments, an effective dose of a composition comprising a PARP1 inhibitor as described herein can be administered to a patient once. In certain embodiments, an effective dose of a composition comprising a PARP1 inhibitor can be administered to a patient repeatedly.

The PARP1 inhibitor can be administered together or sequentially with another agent. Thus, the methods described herein can further comprise administering a second agent and/or treatment to the subject, e.g., as part of a combinatorial therapy. TSC may be treated with rapamycin, vigabatrin, and/or ACTH. LAM may be treated with anti-estrogen therapy, sirolimus, and/or lung transplantation.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following numbered paragraphs:

1. A method of treating a condition associated with mTORC1 hyperactivation, the method comprising administering to a subject having the condition a pharmaceutically-effective amount of a poly(ADP-ribose) polymerase 1 (PARP1) inhibitor.
2. The method of paragraph 1, wherein the condition associated with mTORC1 hyperactivation is selected from the group consisting of tuberous sclerosis complex (TSC), lymphangioleiomyomatosis (LAM), and TSC2-deficient cancer.
3. The method of paragraph 1, wherein the condition associated with mTORC1 hyperactivation is tuberous sclerosis complex (TSC).
4. The method of paragraph 1, wherein the condition associated with mTORC1 hyperactivation is lymphangioleiomyomatosis (LAM).
5. The method of any one of paragraphs 1-4, wherein the PARP1 inhibitor is selected from the group consisting of a small molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof.
6. The method of any one of paragraphs 1-5, wherein the PARP1 inhibitor is selected from the group consisting of 8-hydroxy-2-methylquinazoline-4-one, 3,4-dihydro-5[4-(1-piperindinyl)butoxy]-1(2H)-isoquinoline, 3-aminobenzamide, olaparib, iniparib, rucaparib, veliparib, talazoparib, niraparib, CEP-9722, BGB-290, AG-14361, A-966492 and BMN673.
7. The method of paragraph 5, wherein the PARP1 inhibitor is a small interfering RNA (siRNA).
8. The method of any one of paragraphs 1-7, wherein the subject is a mammal.
9. The method of paragraph 8, wherein the subject is a human.
10. The method of any one of paragraphs 1-9, wherein the administering is systemic.
11. The method of any one of paragraphs 1-9, wherein the administering is local.
12. Use of a poly(ADP-ribose) polymerase 1 (PARP1) inhibitor for the treatment of a condition associated with mTORC1 hyperactivation.
13. The use of paragraph 12, wherein the condition associated with mTORC1 hyperactivation is selected from the group consisting of tuberous sclerosis complex (TSC), lymphangioleiomyomatosis (LAM), and cancer.
14. The use of paragraph 12, wherein the condition associated with mTORC1 hyperactivation is tuberous sclerosis complex (TSC).
15. The use of paragraph 12, wherein the condition associated with mTORC1 hyperactivation is lymphangioleiomyomatosis (LAM).
16. The use of any one of paragraphs 12-15, wherein the PARP1 inhibitor is selected from the group consisting of a small molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof.
17. The use of any one of paragraphs 12-16, wherein the PARP1 inhibitor is selected from the group consisting of 8-hydroxy-2-methylquinazoline-4-one, 3,4-dihydro-5[4-(1-piperindinyl)butoxy]-1(2H)-isoquinoline, 3-aminobenzamide, olaparib, iniparib, rucaparib, veliparib, talazoparib, niraparib, CEP-9722, BGB-290, AG-14361, A-966492, and BMN673.
18. The use of paragraph 16, wherein the PARP1 inhibitor is a small interfering RNA (siRNA).
19. A method of treating TSC2-deficient cancer, the method comprising administering to a subject having the cancer a pharmaceutically-effective amount of a poly(ADP-ribose) polymerase 1 (PARP1) inhibitor.
20. The method of paragraph 19, wherein the PARP1 inhibitor is selected from the group consisting of a small molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof.
21. The method of paragraph 19 or 20, wherein the PARP1 inhibitor is selected from the group consisting of 8-hydroxy-2-methylquinazoline-4-one, 3,4-dihydro-5[4-(1-piperindinyl)butoxy]-1(2H)-isoquinoline, 3-aminobenzamide, olaparib, iniparib, rucaparib, veliparib, talazoparib, niraparib, CEP-9722, BGB-290, AG-14361, A-966492, and BMN673.
22. The method of paragraph 20, wherein the PARP1 inhibitor is a small interfering RNA (siRNA).
23. The method of any one of paragraphs 19-22, wherein the subject is a mammal.
24. The method of paragraph 23, wherein the subject is a human.
25. The method of any one of paragraphs 19-24, wherein the administering is systemic.

26. The method of any one of paragraphs 19-24, wherein the administering is local.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements required for a given embodiment. The term permits the presence of elements that do not materially affect the basic and novel or functional characteristic(s) of that embodiment of the invention.

As used herein, the term "mTORC1 hyperactivation" refers to uncontrolled activation or activity of mTORC1. mTORC1, also known as mammalian target of rapamycin complex 1 or mechanistic target of rapamycin complex 1, is a protein complex that functions as a nutrient/energy/redox sensor and controls protein synthesis. mTORC1 plays a role in activating translation of proteins. In mTORC1 hyperactivation, the activity of mTORC1 can be increased by at least 10%, at least 20%, at least 30%, at least 40%, at least 50%, at least 75%, at least 80%, at least 90%, at least 95%, at least 98%, at least 99% or more as compared to a normal level.

As used herein, the term "TSC2-deficient" refers to decreased TSC2 protein level and/or activity in a cell as compared to a normal cell.

As used herein, the terms "inhibitor of PARP1" or "PARP1 inhibitor" refer to an agent that can decrease the expression level and/or activity of PARP1, e.g. by at least 5%, at least 10%, at least 20%, at least 30%, at least 40%, at least 50%, at least 75%, at least 80%, at least 90%, at least 95%, at least 98%, at least 99% or more. In some embodiments, a PARP1 inhibitor can decrease the level of PARP1 mRNA or the level of PARP1 polypeptide. PARP1 activity can be measured using assays or methods known in the art, such as by assaying the ATP level. In some embodiments, a PARP1 inhibitor can specifically bind an expression product of PARP1. In some embodiments, a PARP1 inhibitor can specifically bind a PARP1 polypeptide. Irreversible or reversible inhibitors of PARP1 can be used in the methods disclosed herein.

The terms "decrease", "reduce", "reduction", or "inhibit" are all used herein generally to mean a decrease by a statistically significant amount. The decrease can be, for example, a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom, the terms "decrease", "reduction", or "inhibition" refer to a statistically significant decrease in such level. Such decrease can be, for example, at least 10%, at least 20%, at least 30%, at least 40% or more, and is preferably down to a level accepted as within the range of normal for an individual without a given disorder.

The terms "increased", "increase", or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, The terms "increased", "increase", "enhance", or "enhanced" refer to a statistically significant increase in such level.

As used herein, the term "antibody" refers to immunoglobulin molecules and immunologically active portions of immunoglobulin molecules, i.e., molecules that contain an antigen binding site that immunospecifically binds an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). In some embodiments, antibody reagents, e.g. antibodies, monoclonal and chimeric antibodies useful in the methods as disclosed herein, can be manufactured using well-known methods, e. g., as described in Howard and Kaser "Marking and Using Antibodies: A Practical Handbook" CRC Press (2006); which is incorporated by reference herein in its entirety.

The terms "antigen-binding fragment" or "antigen-binding domain", which are used interchangeably herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity.

As used herein, the terms "proteins" and "polypeptides" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "disease", "disorder", or "condition" are used interchangeably herein, refer to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailment, malady, disorder, sickness, illness, complaint, or affectation.

As used herein, the terms "treat," "treatment," "treating," or "amelioration" refer to therapeutic treatments, wherein the object is to reverse, alleviate, ameliorate, inhibit, slow down or stop the progression or severity of a condition associated with mTORC1 hyperactivation, e.g. TSC, LAM, or cancer. The term "treating" does not necessarily encompass a cure for a disease or condition associated with mTORC1 hyperactivation. The term "treating" includes reducing or alleviating at least one adverse effect or symptom of a condition, disease or disorder, e.g., a condition associated with mTORC1 hyperactivation. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the extent or amount of cancer size is reduced, or the progression of the condition is halted. The term "treatment" of a disease also includes providing relief from the symptoms or side-effects of the disease (including palliative treatment).

As used herein, the term "pharmaceutical composition" refers to the one or more active agents in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, intralesional, or intratumoral.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local.

The term "statistically significant" or "significantly" refers to statistical significance and generally means a two standard deviation (2SD) or greater difference.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Although methods and materials similar or equivalent to those disclosed herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with the scope of the invention as defined in the claims which follow. The technology disclosed herein is further illustrated by the following examples which in no way should be construed as being further limiting.

Example 1

Rapamycin-Resistant PARP1 Overexpression is a Therapeutic Target in Lymphangioleiomyomatosis (LAM)

The protein products of the TSC1 and TSC2 genes, hamartin and tuberin respectively, interact with TBC1 domain family member 7 (TBC1D7) (11) to form a complex (12) which regulates the state of activation of the mammalian target of Rapamycin complex 1 (mTORC1) (13). Mutation and loss of either gene leads to mTORC1 activation, which has been observed in LAM-derived cells and LAM nodules (4, 14-17). However, TSC2-deficient cells derived from a LAM patient have multiple expression characteristics that are independent of mTORC1 activation (18). We considered the possibility that some of these proteins may contribute significantly to LAM pathogenesis and represent potential therapeutic targets in LAM/TSC-related diseases.

PARP1, the founding and the most studied member of PARP family proteins, is a large abundant nuclear protein activated by DNA damage, which plays a role in chromosomal repair and stability (19, 20). PARP inhibitors have gained increasing popularity as possible chemotherapeutic agents. Studies have documented that BRCA-deficient and PTEN-deficient tumor cells have particular sensitivity to the cytotoxic effect of PARP inhibitors (21-24), suggesting that PARP may be a promising therapeutic target in many forms of cancer.

Here we report that PARP1 expression is upregulated in TSC2-deficient LAM patient-derived cells in vitro, and this is insensitive to treatment with either rapamycin or Torin1 treatment, mTORC1 inhibitors. In vivo, PARP1 expression is abundant in Tsc2-deficient xenograft tumors, in spontaneously-arising renal tumors in Tsc2 heterozygous mice, and in human angiomyolipomas and in LAM nodules. PARP1 inhibitors suppress the growth and induce apoptosis of TSC2-deficient LAM patient-derived cells. Based on these preclinical studies, we propose that PARP1 inhibitors can be therapeutic for women with LAM.

Materials and Methods

DNA Damage Assessment.

H2A.X is required for checkpoint-mediated DNA repair following double-stranded DNA breaks, which results in rapid phosphorylation of H2A.X (Ser139). Cells were fixed in 4% paraformaldehyde for 15 min. Immunofluorescent staining with phospho-γ-H2A.X was performed. Nuclear staining of phospho-γ-H2A.X is the readout of DNA damage.

Gene Expression Analysis.

Re-analysis of previously published expression array data ((GSE16944 (18); GSE10072 (25, 26); GSE19804 (25, 26) and GSE12027 (27)) was performed. Transcript levels of PARPs were compared between TSC2-deficient and TSC2-addback cells, or rapamycin- and vehicle-treated TSC2-deficient cells. Expression levels of PARP1 were compared among HMB45 positive LAM cells collected by laser-capture microdissection from nodular structures in the lungs of 14 LAM cases (LAM) (27), 107 lung adenocarcinomas from the Environment and Genetics in Lung cancer Etiology (EAGLE) study in Italy (25, 26), and 60 paired of lung carcinomas (Lung tumor) and adjacent normal lung tissues (NL) collected from nonsmoking Females in Taiwan (25, 26).

Quantitative RT-PCR was performed using One-Step qRT-PCR Kits in the Applied Biosystems Real-Time PCR System and normalized to beta-actin.

Patient-derived cells including TSC2-null and TSC2 add-back cells were treated with vehicle or PARP1 inhibitors for 24 hr. Total RNA was extracted using the RNeasy mini kit (Qiagen). cDNA was synthesized from 2 μg of total RNA using a high-capacity cDNA reverse transcription kit (Life Technologies) with random primers, according to the manufacturer's protocol. Gene expression was quantified using SYBR green real-time PCR Master Mixes kit (Life Technologies) in the Applied Biosystems Real-Time PCR System and normalized to Tubulin. The primers were used:

```
PARP1
forward:
                                     (SEQ ID NO.: 1)
CCAAGCCAGTTCAGGACCTCAT reverse:
                                     (SEQ ID NO.: 2)
GGATCTGCCTTTTGCTCAGCTTC PARP4
forward:
                                     (SEQ ID NO.: 3)
CATGGCGCTTACCTGATGAGTC reverse:
                                     (SEQ ID NO.: 4)
AACAGTGCCCAGGATGCTGAGT PARP6
forward:
                                     (SEQ ID NO.: 5)
GCCTATGGCAAAGGCATCTACC reverse:
                                     (SEQ ID NO.: 6)
TCTCTGGACCAGCTCATCCTTG PARP8
forward:
                                     (SEQ ID NO.: 7)
ACCGTATGTGAACGGGAGCTGT reverse:
                                     (SEQ ID NO.: 8)
TCCAACGCAGACCTACACATGG PARP9
forward:
                                     (SEQ ID NO.: 9)
GGCAAAGAGGTCCAAGATGCTG reverse:
                                     (SEQ ID NO.: 10)
GCCTCACACATCTCTTCCACGT PARP11
forward:
                                     (SEQ ID NO.: 11)
GAATCTCACCACTGGAAAGCAGC reverse:
                                     (SEQ ID NO.: 12)
CATTCTCCCAGTGTGGTGGCAT PARP12
forward:
                                     (SEQ ID NO.: 13)
CTCTGTCACCAAACCTCCACAC reverse:
                                     (SEQ ID NO.: 14)
GCTACTGCTGACAGTGGTCACA PARP16
forward:
                                     (SEQ ID NO.: 15)
GCATTTCATGGTAGCCGCCTAG reverse:
                                     (SEQ ID NO.: 16)
CAAGTCACTGGTGAGGTAGGTC TIPARP
forward:
                                     (SEQ ID NO.: 17)
GATTCTCAGGAGCACTTGGAAAG reverse:
                                     (SEQ ID NO.: 18)
TGGTGTGGACAGCCTTCGTAGT Tubulin
forward:
                                     (SEQ ID NO.: 19)
GAGGAGATGACTCCTTCAACACC reverse:
                                     (SEQ ID NO.: 20)
TGATGAGCTGCTCAGGGTGGAA
```

Cell Culture and Reagents.

Cell culture media and supplements were from GIBCO (Frederick, Md.). $Tsc2^{-/-}p53^{-/-}$ and $Tsc2^{+/+}p53^{-/-}$ mouse embryonic fibroblasts (MEFs) were developed previously. Mouse expression arrays of $Tsc2^{-/-}p53^{-/-}$ and $Tsc2^{+/+}p53^{-/-}$ MEFs (28) were preformed (29, 30). An immortalized TSC2-deficient human cell line derived from angiomyolipoma of a LAM patient (31), and its corresponding TSC2-rescued control cell line (TSC2-addback cells) has been described previously (18). In brief, patient-derived cells were transfected with pcDNA3.1zeo-hTSC2 or its corresponding empty vector pcDNA3.1zeo (32). Eker rat uterine leiomyoma-derived Tsc2-deficient cells (ELT3) were developed by Howe et al. (33, 34). ELT3 cells were transduced with a retroviral plasmid pMSCVneo-hTSC2 or its corresponding empty vector pMSCVneo (35), and then selected with neomycin for two weeks. Stable clones were characterized for TSC2 expression. Cells were cultured in DMEM/F12 supplemented with 10% fetal bovine serum (FBS), 0.2 µM hydrocortisone, 0.1 nM triiodothyronine, 0.01 µU/ml vasopressin, 1.6 µM FeSO4, cholesterol, human insulin-transferrin-sodium selenite (ITS), 100 ng/ml epidermal growth factor (EGF), 100 µg/ml zeomycin, and 1% penicillin-streptomycin-amphotericin B (PSA). Experiments were performed in triplicate for biochemical analyses. Cells were seeded at a density of $2.5 \times 10^5$ cells/ml in 6-well plates in regular growth media for 24 hr. Media was replaced with serum-free media (Alpha-MEM with 1% PSA) with inhibitors or vehicle. Six or 24 hr later, cell-free conditioned media was collected, and cell lysates were prepared using Radioimmunoprecipitation assay buffer (RIPA) buffer (Boston Bioproducts, Boston, Mass.) supplemented with protease inhibitor cocktail (Roche, Indianapolis, Ind.) and phosphatase inhibitor cocktail (Thermo Scientific, Waltham, Mass.). Protein concentration was determined using Bradford assay (BioRad Laboratories Inc. Hercules, Calif.).

Antibody.

Antibody clones used: PARP1 (#9532, residues surrounding Gly623), Phospho-Histone H2A.X (Ser129) (#9718, Rabbit mAb 20E3), Phospho-56 (Ser235/236) (#4858, D57.2.2E), S6 (#2317), Phospho-Akt (Ser473) (#9271), Akt (#9272), Raptor (#2280), mTOR (#2972) (Cell Signaling Technology); PAR (#4335-MC-100, Trevigen); Tuberin (TSC2) (#sc-893, C20), α-Actin (#sc-32251) (Santa Cruz).

PARP Inhibitors.

NU1025 (8-Hydroxy-2-methylquinazoline-4-one), DPQ (3,4-Dihydro-5[4-(1-piperinidinyl)butoxy]-1(2H)-isoquinoline), and Olaparib were purchased from EMD Chemicals.

Cell Viability Assay.

Cells were seeded at a density of $5 \times 10^4$/ml in 96-well plate for 24 hr, and then treated with inhibitors or vehicle control for 24 hr. Cell numbers were quantified using CyQuant (Invitrogen, Carlsbad, Calif.). Values are expressed as mean±SEM; n=8/group. *P<0.05; Student's t-test.

Cell Death Assay.

Cells were treated with PARP1 inhibitors for 24 hr. $H_2O_2$ was added for 1 hr. Cells were harvested and subjected to Annexin V:FITC staining (BD). Flow cytometry analysis was performed.

Animal Studies.

9-10 month-old $Tsc2^{+/-}$ C57Bl6 mice (36) were treated with 3 mg/kg rapamycin or vehicle for three doses. Mice were sacrificed and kidneys were harvested. Visible renal tumors were extracted macroscopically and normal appearing parts of kidneys were collected as controls. For xenograft tumor study, $2 \times 10^6$ ELT3-V3 (TSC2-null) or ELT3-T3 (TSC2-reexpressing) cells were inoculated bilaterally into the posterior back region of female intact CB17-SCID mice (Taconic) as previously described (37, 38). Seven weeks post cell inoculation, tumors were harvested. Tissues were homogenized in RIPA buffer supplemented with protease and phosphatase inhibitors, and centrifuged at 14,000 RPM for 10 min at 4° C. Supernatant extracts were assayed for protein concentration by Bradford assay.

Immunohistochemistry.

Histology sections were prepared from mouse kidneys harvested from 6 months old Tsc2 mice after 10% formalin fixation and cutting into five 1-2 mm sections in cassettes. Immunohistochemistry (IHC) was performed on paraffin-embedded 10 µm-sections using antibodies against PARP1 (Cell Signaling, Danvers, Mass.). Slides were deparaffinized and antigen retrieval was performed using Dako Target Retrieval Solution pH 6 (Dako, Carpinteria, Calif.). Sections were stained by the immunoperoxidase technique using DAB substrate (Dako EnVision System HRP) and counterstaining with hematoxylin. After staining, slides were viewed on a Nikon Eclipse E400 microscope, and images captured using Spot Insight digital camera with Spot software (Diagnostic Instruments, Sterling Heights, Mich.).

Western Blotting.

Histology sections were prepared from mouse kidneys harvested from 6 months old $Tsc2^{+/-}$ mice after 10% formalin fixation and cutting into five 1-2 min sections in cassettes. Immunohistochemistry (IHC) was performed on paraffin-embedded 10 µm-sections using antibodies against PARP1 (Cell Signaling, Danvers, Mass.). Slides were deparaffinized and antigen retrieval was performed using Dako Target Retrieval Solution pH 6 (Dako, Carpinteria, Calif.). Sections were stained by the immunoperoxidase technique using DAB substrate (Dako EnVision System HRP) and counterstaining with hematoxylin. After staining, slides were viewed on a Nikon Eclipse E400 microscope, and images captured using Spot Insight digital camera with Spot software (Diagnostic Instruments, Sterling Heights, Mich.).

RNA Interference.

Small-interfering RNA (siRNA) Silencer siRNA constructs against Raptor (s33216) 5'-CCATCGGTGCAAATT-TACA-3' (SEQ ID NO.: 21), mTOR (s603) 5'-CATTCG-CATTCAGTCCAT A-3' (SEQ ID NO.: 22), or nonsense negative control (NC) were purchased from Ambion (Austin, Tex.), and used as suggested by the manufacturer. Briefly, 30 nM Silencer siRNA constructs were incubated in Opti-MEM (Invitrogen, Carlsbad, Calif.) with NeoFX transfection agent. This mixture was then applied to 12-well plates with $1 \times 10^5$ cells/well in Opti-MEM for 24 hr. Media was replaced with 1 ml/well of serum-free media and incubated for another 24 hr before collection of cell-free media and cell lysates as described above.

Statistical Analyses.

Statistical analyses were performed using Student's t-test when comparing two groups. Results are presented as means±SD.

Results

DNA damage repair mechanism is dysfunctional in cells lacking TSC2. It has been reported that the cellular levels of reactive oxygen species (ROS) were significantly higher in TSC2-null rat uterine-derived ELT3 cells compared with TSC2 addback cells (39). Here, we found that the levels of ROS were 36% higher in TSC2-deficient patient-derived cells relative to TSC2-addback cells (p<0.01) (FIG. 1A), consistent with the published data (39). Considering ROS as a main contributor of oxidative DNA damage (40, 41), we next examined whether TSC2 regulates ROS-triggered DNA damage using phospho-γH2A.X as the readout. Immunofluorescent staining of phospho-γH2A.X was more prominent in TSC2-reexpressing cells relative to TSC2-deficient cells (FIG. 1B). Notably, rapamycin treatment did not affect phospho-γH2A.X staining in TSC2-deficient cells (FIG. 1B). Together, these data indicate a dysfunctional DNA damage repair mechanism in cells lacking TSC2.

Identification of PARP1 Upregulation in TSC2-Deficient Cells.

PARP family members play a critical role in repair of single-stranded DNA breaks (42, 43). We hypothesized that TSC2 regulates the function of PARPs in cells under oxidative stress. To determine whether PARP1 expression is altered in cells lacking TSC2, we performed expression array analysis using our previously published data sets (18).

Figures 2A, 2B, 2C, 2D:
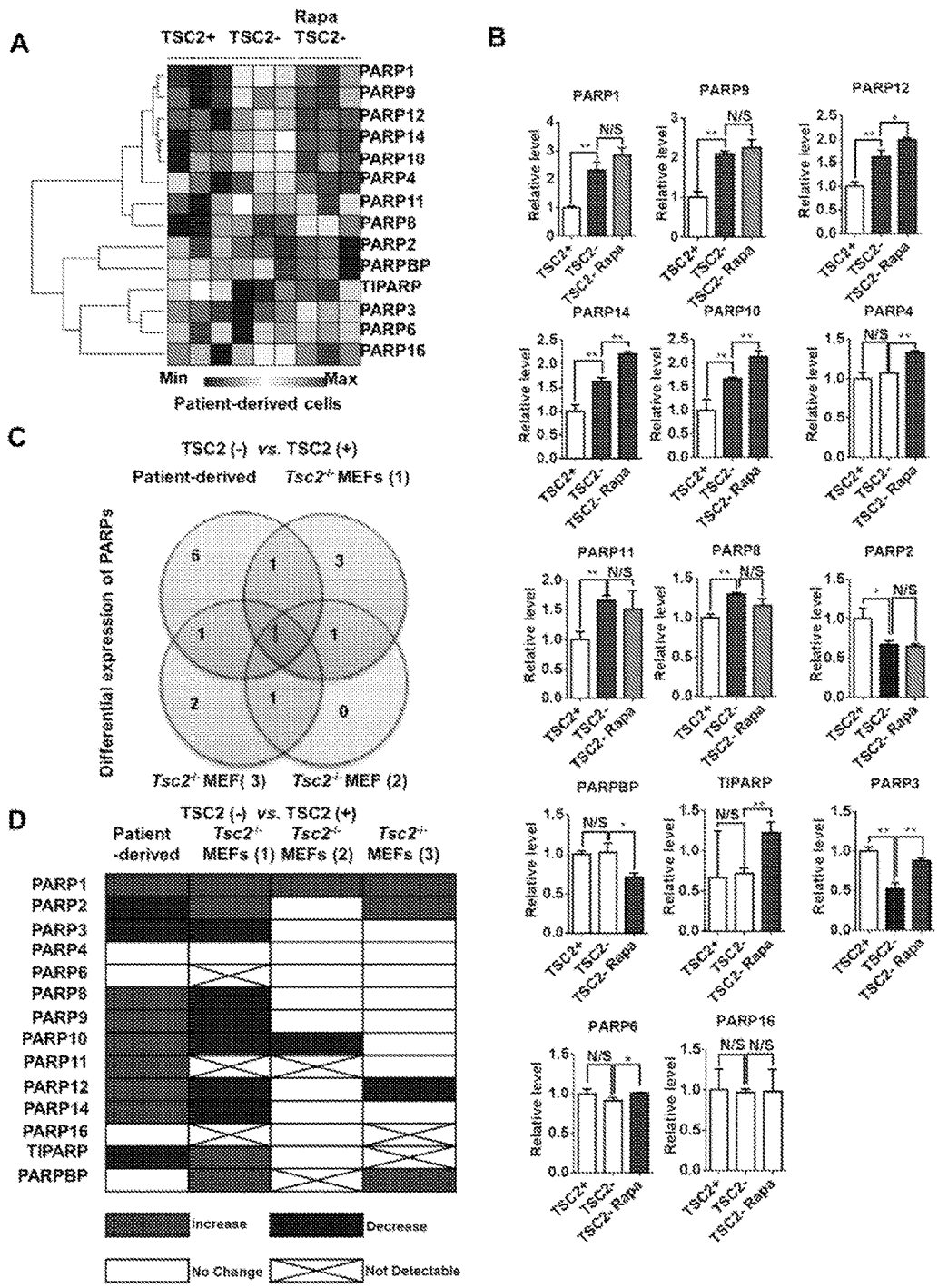
FIGS. 2A-2D describe experimental data demonstrating that TSC2 negatively regulates the expression of PARP1 in vitro.
Figure 8:
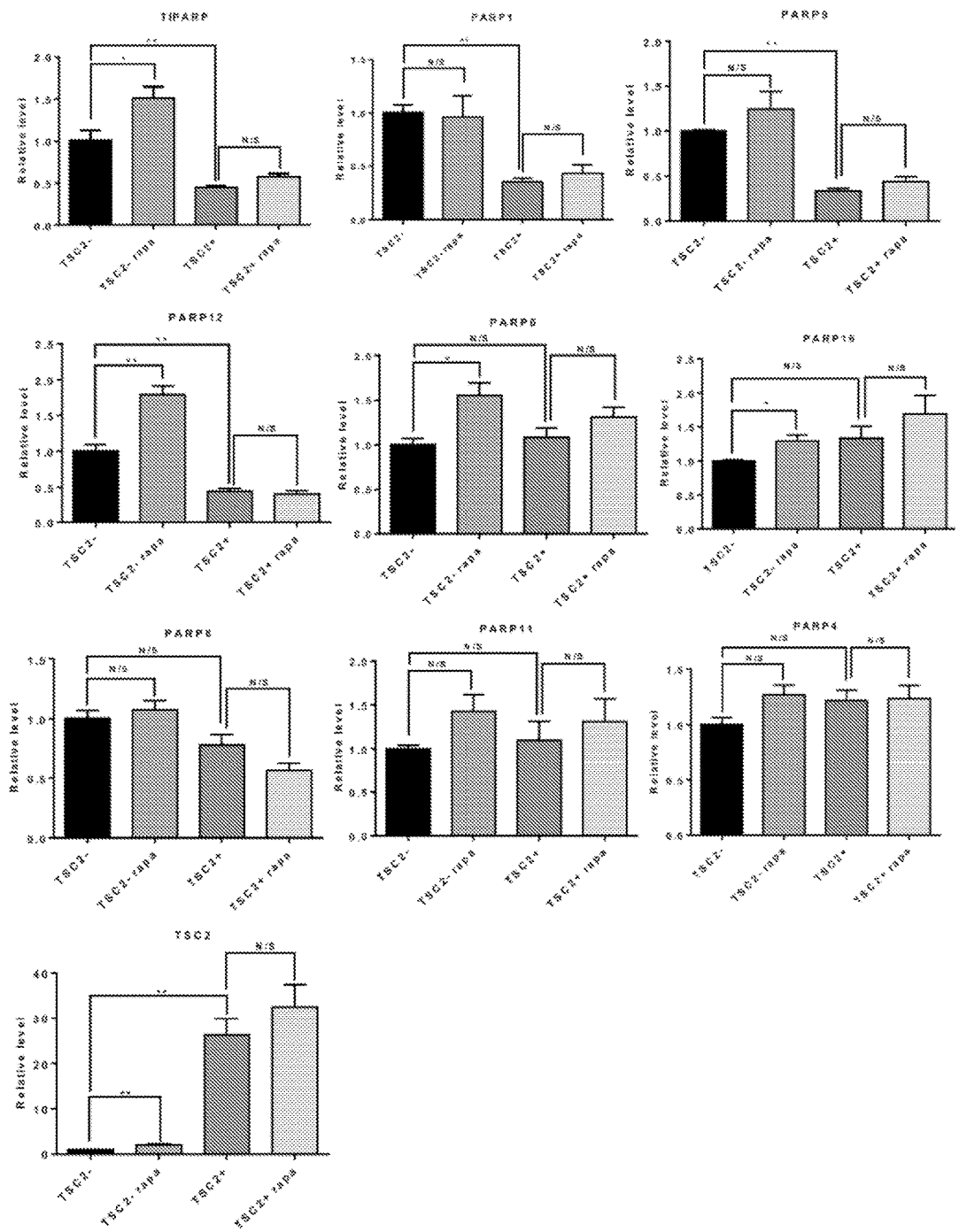
FIG. 8 is a set of graphs showing identification of PARP family members regulated by TSC2 and mTOR. Patient-derived TSC2-deficient and TSC2 add-back cells were treated with vehicle or 20 nM rapamycin for 24 hr. Transcript levels of PARPs were quantitated using real-time RT-PCR.

Gene set enrichment analysis showed that the transcript levels of ten PARP family members, including PARP1, PARP8, PARP9, PARP10, PARP11, PARP12, and TIPARP, were significantly higher in TSC2-deficient (TSC2−) LAM patient-derived cells compared to TSC2-addback cells (TSC2+) (FIG. 2A). Interestingly, rapamycin treatment did not affect the expression of PARPs overall, and in some cases appeared to increase expression of some PARP isoforms (PARP1, PARP9, PARP12, and PARP14) (FIG. 2A, 2B). Next, we performed quantitative real-time PCR to validate our array findings. The transcript levels of PARP1, PARP9, PARP12, and TIPARP were higher in TSC2-deficient patient-derived cells relative to TSC2-reexpressing cells (FIG. 8).

To determine which PARP member(s) is critical in the context of TSC2-deficiency, we analyzed three additional publicly available expression array data sets. The transcript levels of 12 PARP members were altered in $Tsc2^{-/-}$ MEFs compared to $Tsc2^{+/+}$ MEFs from data sets GSE21755, GSE27982 (29), and GSE28021 (29), respectively. Notably, the cross comparison of differently expressed PARPs identified PARP1 as the commonly altered gene in TSC2-deficient cells relative to TSC2-expressing cells from all expression array data sets (FIG. 2C, 2D).

Figure 9:
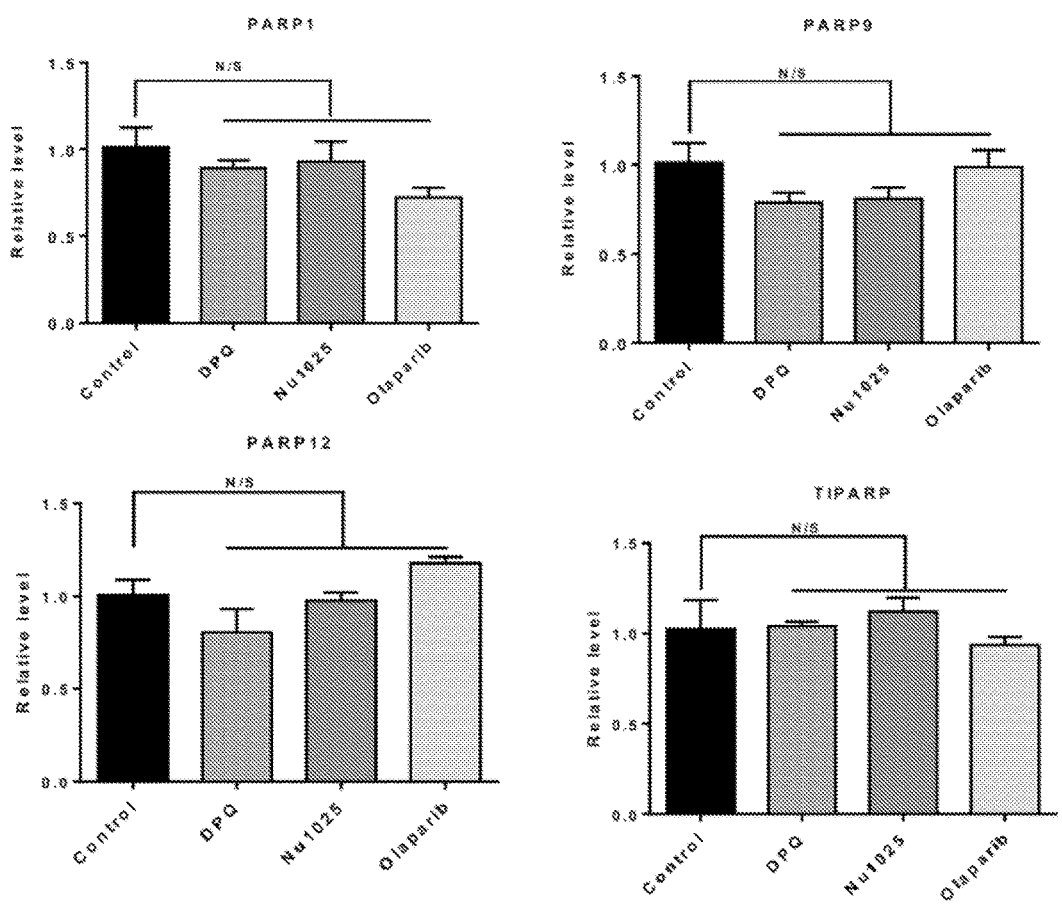
FIG. 9 is a set of graphs demonstrating that PARP1 inhibitors do not affect transcript levels of PARPs in TSC2-deficient patient-derived cells. Patient-derived TSC2-deficient cells were treated with 10 μM DPQ, 10 μM Nu1025, 10 μM Olaparib, or vehicle for 24 hr. Transcript levels of PARP1, 9, 12 and TIPARP were quantitated using real-time RT-PCR.

To examine the impact of PARP inhibitors on the transcript levels of PARPs, we treated TSC2-deficient patient-derived cells with PARP inhibitors for 24 hr. DPQ is a potent inhibitor of PARP1 (IC50=40 nM) (44), although much less potent against PARP2 (45). Nu-1025 is potent inhibitor of PARP1 (IC50=400 nM) (46, 47). Olaparib (AZD2281) is a selective inhibitor of PARP1/2 (IC50=1-5 nM) (48). Quantitative real-time PCR analysis showed that the transcript levels of PARP1, PARP9, PARP12 or TIPARP were not significantly altered by PARP inhibitor treatment (FIG. 9).

TSC2 Negatively Regulates PARP1 Expression in an mTOR-Independent Manner In Vitro.

Figures 3A, 3B, 3C, 3D, 3E, 3F:
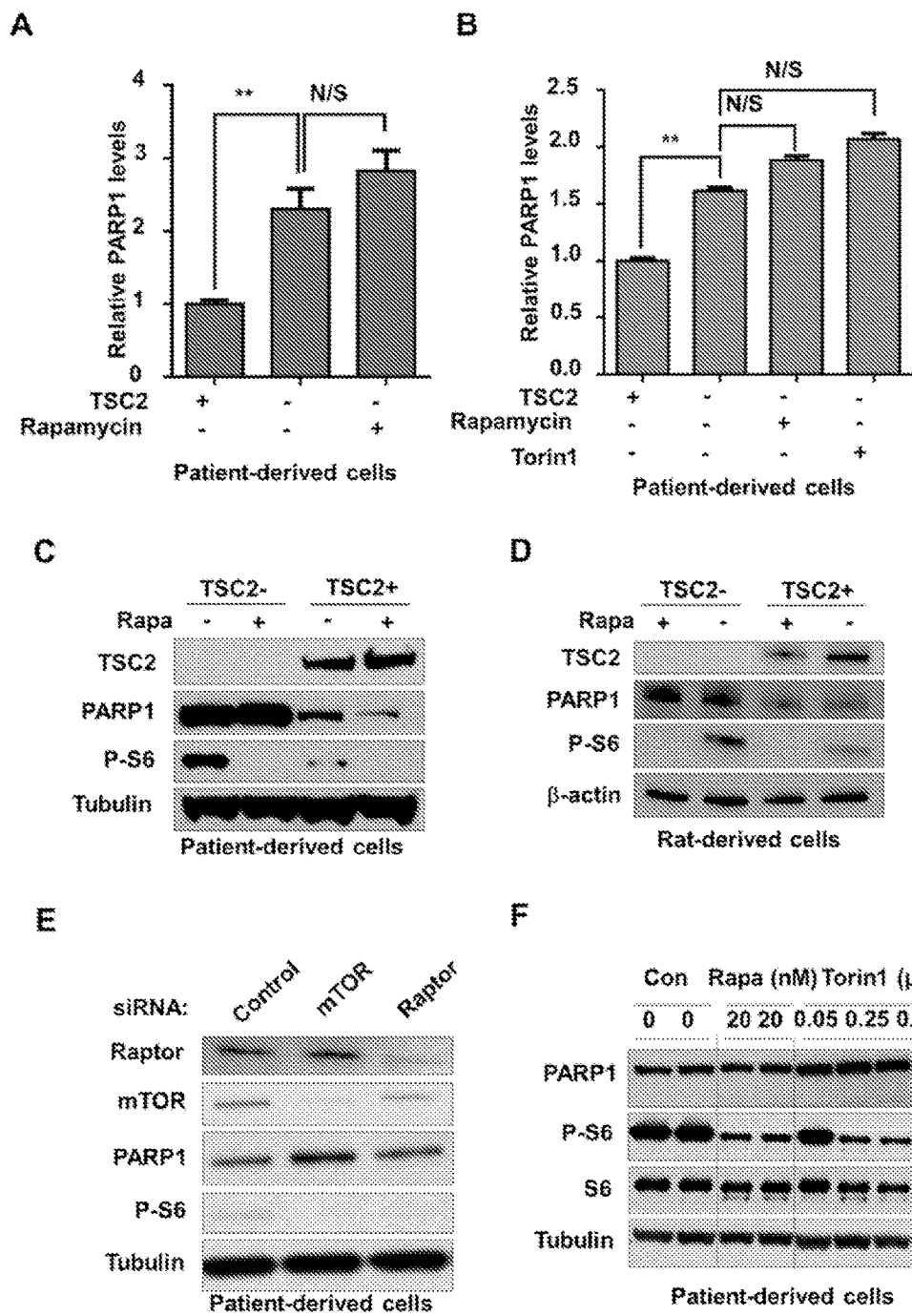
FIGS. 3A-3F describe experimental data demonstrating that TSC2 negatively regulates the expression of PARP1 in vitro.

To define the molecular mechanisms responsible for PARP1 overexpression, we re-analyzed our previous expression array of TSC2-deficient LAM patient-derived cells (18) and found that PARP1 expression was increased by 2.3 fold in TSC2-deficient LAM patient-derived cells compared to TSC2-addback cells (P<0.05; FIG. 3A). Interestingly, rapamycin treatment did not affect the level of PARP1 (FIG. 3A). To validate the findings of the expression array, we first performed real-time PCR analysis. TSC2-deficient LAM patient-derived cells exhibited a two-fold increase of PARP1 (P<0.01; FIG. 3B). Importantly, rapamycin treatment did not alter the levels of PARP1, consistent with the changes identified in the expression array study (18) (FIG. 3B). Torin 1 is a potent ATP-competitive mTORC1 and mTORC2 inhibitor. We treated cells with Torin 1 for 24 hr. Interestingly, Torin 1 treatment did not affect PARP1 expression (FIG. 3B). Our data suggest that upregulation of PARP1 expression is independent of mTOR.

We next assessed the protein levels of PARP1 using western blot analysis. PARP1 protein levels were higher in TSC2-deficient LAM patient-derived cells compared with TSC2-addback cells (FIG. 3C). Rapamycin treatment suppressed phosphorylation of the ribosomal protein p70S6 (S6), but did not affect PARP1 levels (FIG. 3C). Similar observations were made in rat uterine leiomyoma-derived ELT3 cells (33, 34) expressing empty vector (TSC2−) relative to TSC2-reexpressing cells (TSC2+) (FIG. 3D). Collectively, our data show that TSC2 negatively regulates the expression of PARP1 in a rapamycin-insensitive manner.

Rapamycin only suppresses part of mTORC1 activity, and has little effect on mTOR complex 2 (mTORC2) (49, 50).

Therefore, we tested whether PARP1 overexpression in TSC2-deficient cells may be due to other mTOR-associated pathways. mTOR or raptor (Rap, a component of mTORC1) was depleted by siRNA, resulting significant suppression of phospho-S6 compared to non-targeting siRNA control (NC) (FIG. 3E). However, PARP1 remained highly expressed in TSC2-deficient cells under mTOR or raptor siRNA knockdown (FIG. 3E). To examine whether Torin 1 treatment affects PARP1 protein levels in greater detail, we performed a dose-response of Torin 1 and found that Torin 1 from 0.25 nM to 1 µM did not affect on PARP1 protein levels in TSC2-deficient LAM patient-derived cells (FIG. 3F). Our data suggest that PARP1 overexpression is independent of mTORC1 or other mTOR components in cells lacking TSC2.

TSC2 Negatively Regulates PARP1 Expression In Vivo.

Figure 4A:
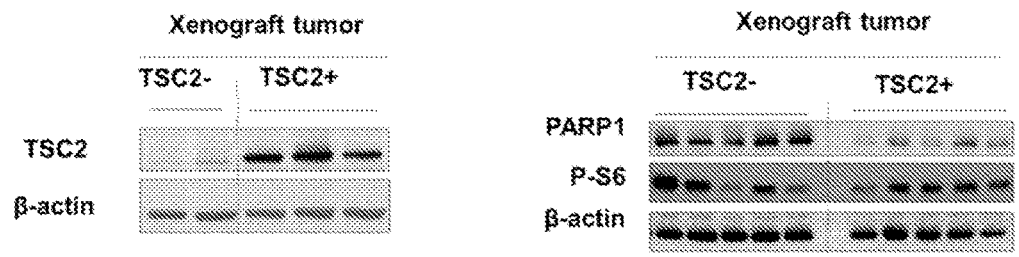
FIGS. 4A-4C describe experimental data demonstrating that TSC2 negatively regulates the expression of PARP1 in vivo.
Figure 4B:
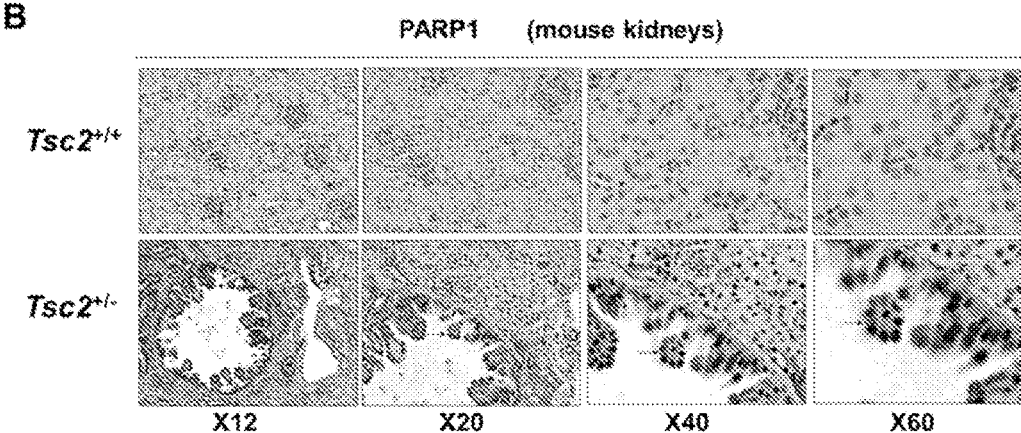

To determine whether TSC2 regulates PARP1 expression in vivo, we first used xenograft tumors from mice inoculated with TSC2-deficient ELT3-V3 (TSC2−) cells and TSC2-reexpressing ELT3-T3 (TSC2+) cells. Immunoblot analysis showed that TSC2 was detected in ELT3 (TSC2+) xenograft tumors but not in ELT3 (TSC2−) tumors (left panel, FIG. 4A). PARP1 protein levels were markedly higher in TSC2− xenograft tumors with increased phosph-S6 compared to TSC2+ tumors (FIG. 4A). We next examined spontaneously arising renal cystadenomas, commonly observed in $Tsc2^{+/-}$ transgenic mice (36). Tumors exhibited abundant accumulation of PARP1 in the nucleus of tumor cells (FIG. 4B). Adjacent normal kidney tubule cells were moderately positive for PARP1, but glomeruli were negative for PARP1 in $Tsc2^{+/-}$ mice and in $Tsc2^{+/+}$ (FIG. 4B).

Figure 4C:
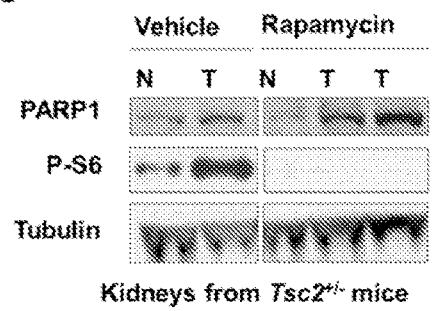

To confirm these observations and to test the role of mTORC1 in PARP1 overexpression in vivo, $Tsc2^{+/-}$ mice were subjected to short-term treatment with rapamycin (6 mg/kg every 2 days for one week) or vehicle control before harvesting renal tumors for immunoblotting. Renal tumors from a $Tsc2^{+/-}$ mouse treated with vehicle control exhibited high phospho-S6, as expected, reflecting mTORC1 activation compared to adjacent normal kidney tissue. Importantly, PARP1 expression is also noticeably higher in tumor relative to adjacent normal kidney (FIG. 4C). Renal tumors from a $Tsc2^{+/-}$ mouse treated with rapamycin exhibited suppressed phospho-S6, confirming effective mTORC1 inhibition. In contrast, the levels of PARP1 expression remained high in two renal tumors compared to adjacent normal kidney tissues (FIG. 4C). These data support the model that TSC2-deficiency leads to rapamycin-insensitive upregulation of PARP1.

PARP1 Overexpression is Evident in Pulmonary LAM Nodules.

Figures 5A, 5B, 5C, 5D:
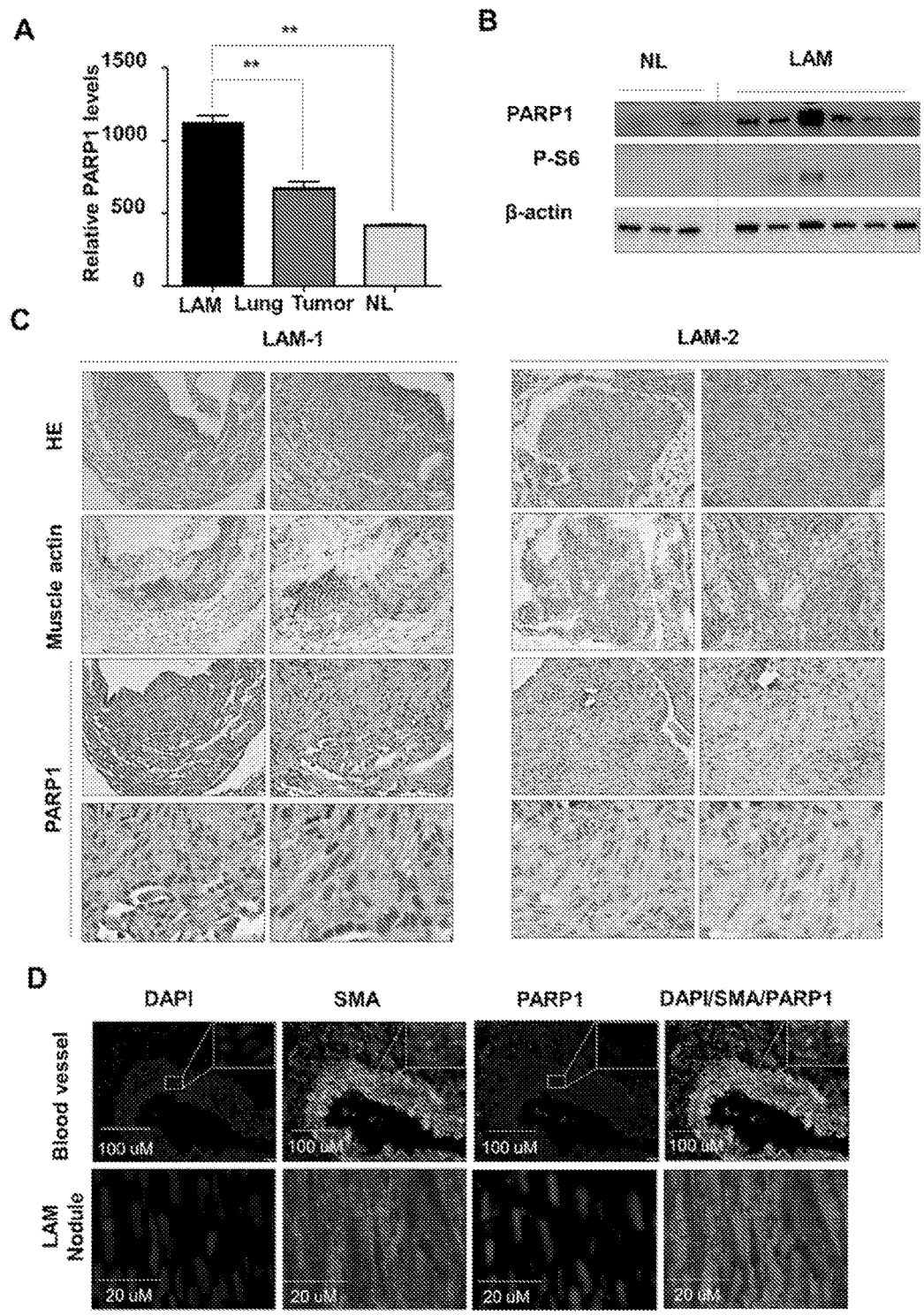
FIGS. 5A-5D describe experimental data demonstrating that PARP1 overexpression is evident in pulmonary LAM.

We then examined whether our in vitro and in vivo findings were relevant to human LAM. Accordingly, we analyzed publicly available expression array data sets from LAM cells collected by laser-capture microdissection from LAM nodules (GEO data set GSE12027) (27), lung cancer/tumor (GEO data set GSE10072 and GSE19804) (25, 26), and control lungs (GEO data set GSE10072 and GSE19804) (25, 26). LAM nodule cells expressed higher levels of PARP1 transcript compared to control lungs (NL) (P<0.01; FIG. 5A). Furthermore, immunoblotting analysis showed that phospho-S6 positive LAM lungs exhibited elevated levels of PARP1 protein relative to control lungs (NL) (FIG. 5B). Moreover, immunohistochemistry showed that nuclear accumulation of PARP1 is abundant in smooth muscle actin positive LAM nodules (FIG. 5C). Furthermore, we performed dual immunostaining of smooth muscle α-actin and PARP1 in LAM lung tissues. Smooth muscle α-actin positive cells exhibited prominent nuclear localization of PARP1, indicating that PARP1 is indeed upregulated in LAM cells but not in pulmonary artery smooth muscle cells (FIG. 5D).

Pharmacologic Inhibition of PARP1 Selectively Suppresses the Growth of TSC2-Deficient Cells.

Figures 6A, 6B, 6C, 6D:
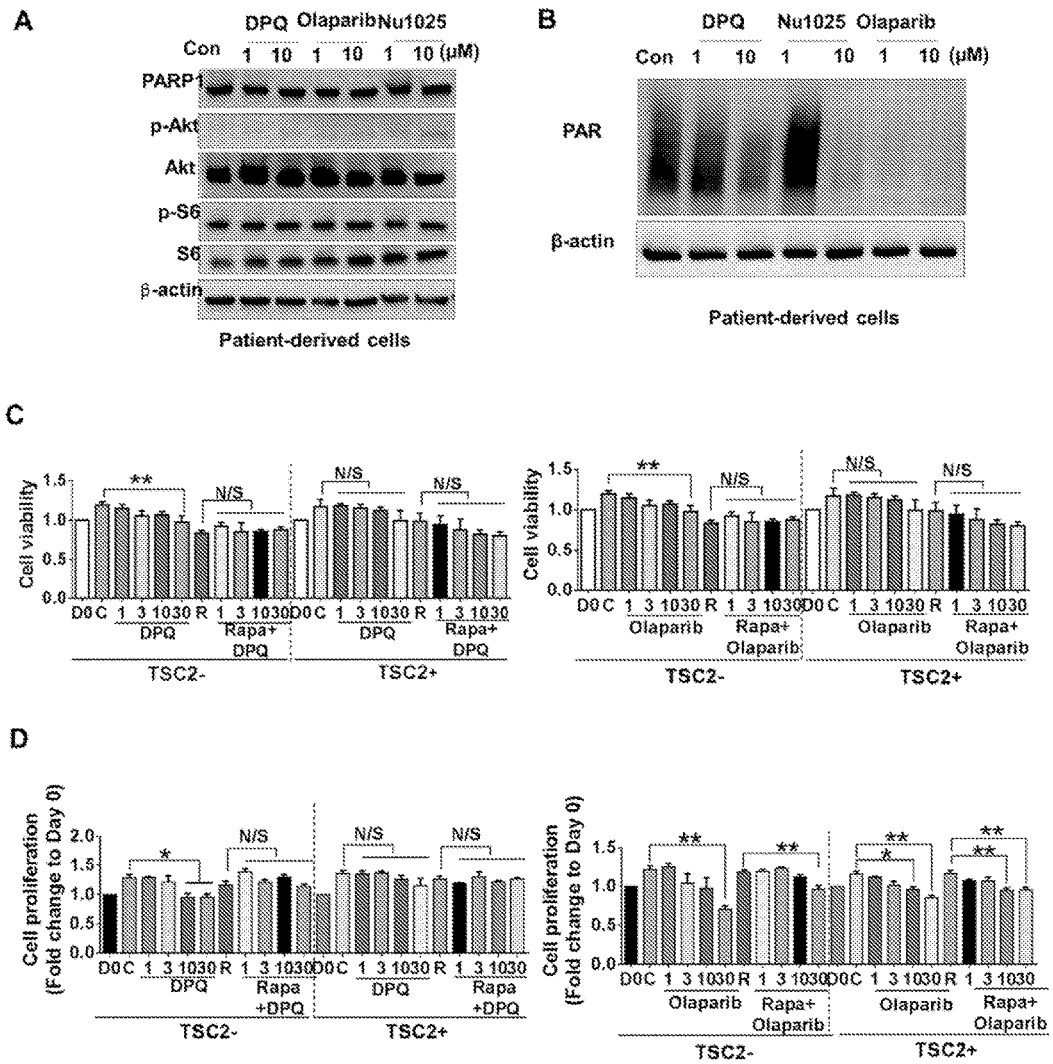
FIGS. 6A-6D describe experimental data demonstrating that inhibition of PARP1 suppresses the growth of TSC2-deficient cells.

Having shown that mTORC1 inhibition has no effect on PARP1 expression, we asked whether PARP1 suppression could affect mTORC1 activation in TSC2-deficient cells. As expected, rapamycin treatment suppressed phosphorylation of S6 (S240/244) and increased phosphorylation of Akt (S473) (FIG. 6A), consistent with previous reports of a negative feedback inhibition between mTORC1 and Akt (28, 51, 52). Interestingly, DPQ and NU1025, two PARP inhibitors, did not affect phosphorylation of S6 at high dose at 10 nM or 100 nM, respectively (FIG. 6A). Importantly, NU1025 at 100 nM modestly increased phosphorylation of Akt (S473), suggesting that inhibition of PARP1 has no impact on mTORC1 activation in TSC2-deficient cells, although possible interactions between Akt and PARP1 may warrant future studies.

To assess the efficacy of PARP inhibitors on PARP1 expression, we treated patient-derived cells with DPQ (1 and 10 nM) and NU1025 (10 and 100 nM) for 24 hr. Immunoblot analysis with PARP1 showed that PARP inhibitors did not affect the protein levels of PARP1 (FIGS. 6A, 6B), suggesting that the mechanism of action of PARP inhibitors is unlikely the suppression of PARP1 expression.

PARP1 activity is to catalyze the formation of Poly(ADP-Ribose) (PAR). To examine whether PARP1 inhibitors affect the activity of PARP1, we treated TSC2-deficient patient-derived cells with DPQ, NU1025, or Olaparib, and then performed immunoblot analysis for PAR. Treatment with 10 μM DPQ, 10 μM NU1025, or 1 μM and 10 μM Olaparib, markedly decreased the levels of PAR compared with the control (FIG. 6B), indicating that PARP inhibitors suppress the activity rather than the expression of PARP1, consistent with other findings (53).

We then tested the possible dose-dependent cytotoxic effect of PARP1 inhibitors, DPQ (1 μM-30 μM) and Olaparib (1 μM-30 μM), in TSC2-deficient patient-derived cells and their TSC2-reexpressing counterparts, and performed side-by-side comparison of the drug effects in cell viability. 30 μM DPQ or Olaparib selectively decreased cell viability by 15-40% (p<0.01) (FIG. 6C) and proliferation (FIG. 6D) of TSC2-deficient cells. Importantly, TSC2-addback cells were resistant to Olaparib and DPQ treatment (FIG. 6C, D). We noted that rapamycin treatment up to 24 hr had no appreciable cytotoxic effect on cell growth (FIG. 6C, D).

To determine whether mTORC1 and PARP1 pathways intersect, we treated TSC2-deficient LAM patient-derived cells with rapamycin plus PARP1 inhibitors DPQ or Olaparib, and then measured cell viability using MTT assay, cell proliferation using crystal violet staining, and cell death using PI exclusion assay. PARP1 inhibition marginally decreased cell viability (FIG. 6C) and cell proliferation (FIG. 6D). Interestingly, combination treatment of rapamycin and PARP1 inhibitor did not further decrease cell viability (FIG. 6C) or cell proliferation (FIG. 6D), compared with PARP1 inhibitor alone. These data indicate that there is no synergistic effect between rapamycin and PARP1 inhibitors in the growth of TSC2-deficient LAM patient-derived cells.

Pharmacologic Inhibition of PARP1 Promotes Apoptosis of TSC2-Deficient Cells.

Figures 7A, 7B, 7C, 7D:
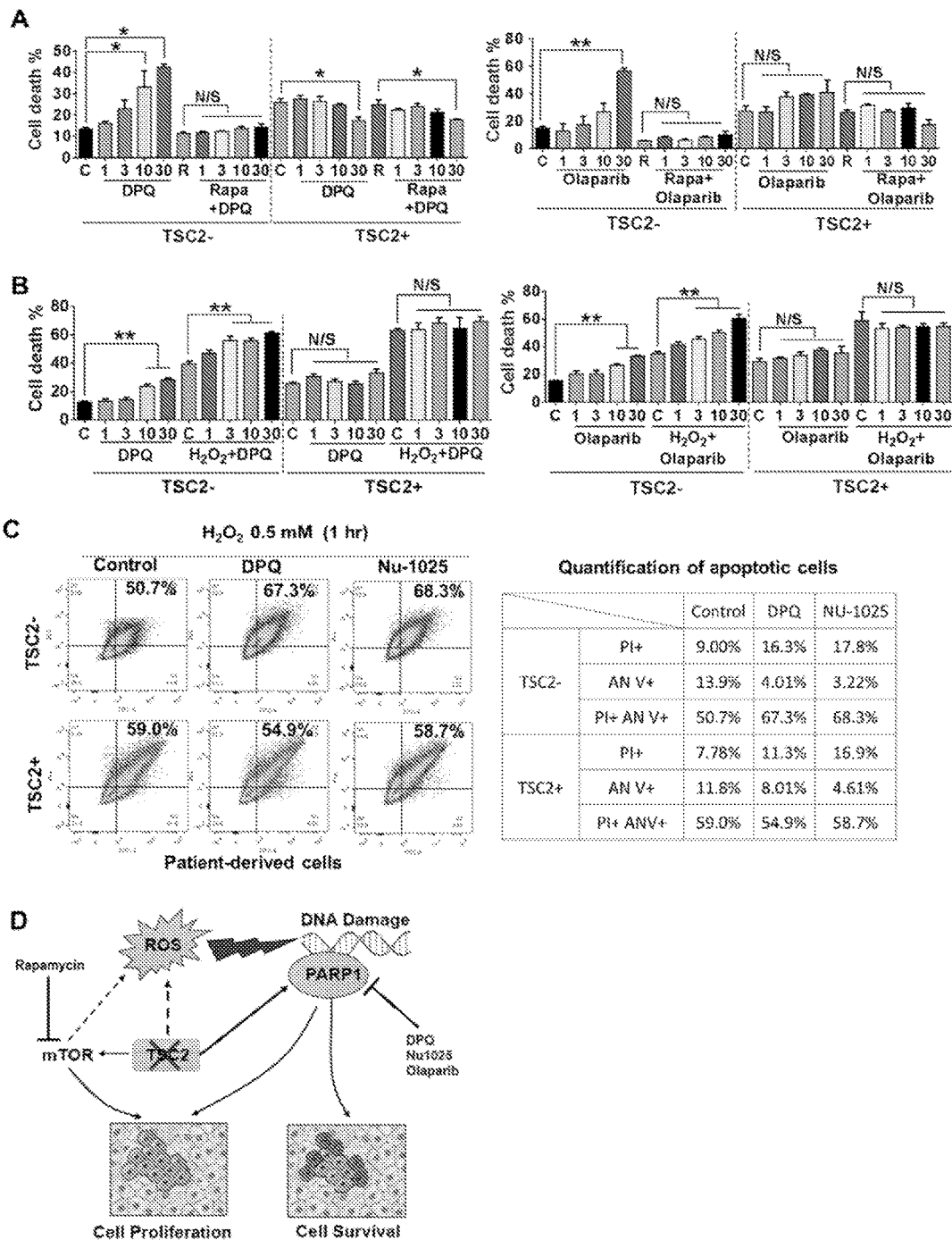
FIGS. 7A-7D describe experimental data demonstrating that inhibition of PARP1 promotes apoptosis of TSC2-deficient cells.

It has been reported that PARP1 plays a role in repair of oxidative stress induced DNA damage and cell survival (54). To examine whether PARP1 inhibitors affect cell survival, TSC2-deficient and TSC2-reexpressing patient-derived cells were treated with 10 and 30 μM DPQ, or 30 μM Olaparib. Both drugs selectively killed TSC2-deficient cells without affecting the survival of TSC2-reexpressing cells (FIG. 7A). Next, we treated TSC2-deficient patient-derived cells and TSC2-reexpressing cells with 1-30 μM DPQ or Olaparib in the presence of hydrogen peroxide ($H_2O_2$). $H_2O_2$ treatment alone induced apoptosis to the same extent in both TSC2-deficient and TSC2-reexpressing cells (FIG. 7B). Interestingly, in the presence of $H_2O_2$, 3-30 μM DPQ or Olaparib significantly induced the death of TSC2-deficient cells by ~50% (p<0.01) (FIG. 7B). Notably, PARP inhibitors plus rapamycin treatment did not further induce cell death, indicating no synergistic effect between rapamycin and PARP1 inhibitors in the survival in TSC2-deficient LAM patient-derived cells.

To quantify the levels of cell death triggered by $H_2O_2$ exposure in TSC2-deficient patient-derived cells, we performed a cytometric Annexin V and PI (Propidium Iodide) assay. TSC2-deficient cells treated with DPQ exhibited 33% higher population of apoptotic cells compared to Control (67.3% vs. 50.7%) (FIG. 7C). In addition, TSC2-deficient cells treated with Nu1025 showed 35% higher population of apoptotic cells compared to Control (68.3% vs. 50.7%) (FIG. 7C). Together, these data indicate that inhibition of PARP1 suppresses the growth and promotes cell death of LAM patient-derived cells under oxidative stress.

DISCUSSION

PARP1 is activated by DNA damage and plays a role in chromosomal repair and stability (19, 20). We report here for the first time that TSC2-deficient cells demonstrate increased PARP1 expression in vitro and in vivo, and that the increase is rapamycin insensitive and mTOR independent. Furthermore, TSC2-deficient cells exhibited higher cytotoxicity to PARP inhibition compared to TSC2-addback cells.

Our data suggest that PARP1 upregulation is likely a direct consequence of TSC2 loss because in several human or animal-derived TSC2-deficient cells/tissues, PARP1 upregulation can be documented. PARP1 expression can only be suppressed by TSC2 reconstitution and is not affected by mTOR inhibition from rapamycin or Torin 1 treatments, or mTOR or raptor siRNA interference. Therefore TSC2 deficiency upstream of mTOR pathway is the culprit leading to PARP1 upregulation (FIG. 7D).

Several studies have documented possible mTORC1-independent effects in cells lacking TSC1/TSC2. B-Raf kinase activity is reduced in TSC2-deficient cells due to Rheb-GTP activation which interacts with B-Raf and inhibits its activity in an mTORC1-independent manner (56, 57). Tsc2-null MEFs (murine embryonic fibroblasts) exhibit reduced Akt kinase activation partially due to impaired mTORC2 activity (16). Tsc1- or Tsc2-null MEFs have a higher percentage of cilium-containing cells compared to the respective controls, and rapamycin treatment has no effect on this observation (17). We previously found that matrix metalloproteinase (MMP) over-expression in TSC2-deficient cells is resistant to rapamycin suppression of mTORC1 (18). Recently, we found that TSC2 negatively regulates cyclooxygenase-2 (COX-2) expression and prostaglandin production in a rapamycin-insensitive but mTORC2-dependent manner (38). The current report adds to the accumulating evidence that mTORC1-independent aberrantly regulated pathways contribute to TSC-related diseases, and that rapamycin alone may be insufficient as a clinical therapy.

In this study, we found that the levels of ROS were higher in TSC2-deficient patient-derived cells relative to TSC2-addback cells, consistent with the previous findings in Tsc2-null rat-derived ELT3 cells (39). We also found that the molecular marker of DNA damage γH2A.X was more prominent in TSC2-reexpressing cells relative to TSC2-deficient cells, indicative of a dysfunctional DNA damage repair mechanism in cells lacking TSC2. ROS is a main contributor of oxidative DNA damage (40, 41). PARP family members play a critical role in repair of single-stranded DNA breaks (42, 43). Our findings of PARP1 upregulation and efficacy of PARP inhibitor in limiting the survival of LAM patient-derived cells indicate a therapeutic benefit of targeting PARP1 for the treatment of LAM.

Compared to TSC2-positive cells, TSC2-deficient cells exhibited higher sensitivity to the cytotoxic effect of PARP1 inhibition. Rapamycin did not enhance, and actually could antagonize this effect. Therefore, our data suggest that unsuppressed mTOR activity from loss of TSC2 may not be critical for the survival of TSC2-deficient cells and that PARP1 upregulation is important for the viability of TSC2-deficient cells with mTOR hyperactivation. These data have implications in oncologic therapy. It is contemplated that PARP1 inhibitors can be particularly effective in cancer types exhibiting increased mTOR activity; thus, the status of mTOR activity may serve as a predictive biomarker for PARP1 inhibitors.

The Multicenter International LAM Efficacy of Sirolimus Trial (The MILES trial) demonstrated that the mTORC1 inhibitor Sirolimus stabilizes lung function and improves quality of life in women with LAM. However, upon drug withdrawal, lung function decline resumed (58), indicating that mTORC1 inhibitor has a cytostatic but not cytotoxic effect in LAM cells. We report here promising pre-clinical results using PARP1 inhibitors which specifically suppress the growth and survival of TSC2-deficient LAM patient-derived cells. In conclusion, we report that PARP1 expression is elevated in TSC2-deficient patient-derived cells compared to TSC2-reexpressing cells, and that PARP inhibitors selectively suppress the proliferation of TSC2-deficient cells. Our data add to a growing list of FDA-approved agents with potential efficacy in LAM including simvastatin (59), chloroquine (60, 61), doxycycline (62), and aspirin (38). It is contemplated that PARP1 inhibitors can provide a novel opportunity for the therapy of LAM.

REFERENCES

1. Krymskaya V P. Treatment option(s) for pulmonary lymphangioleiomyomatosis: progress and current challenges. Am J Respir Cell Mol Biol; 46(5):563-565.
2. McCormack F X, Panos R J, Trapnell B C, editors. Molecular Basis of Pulmonary Disease Insights from Rare Lung Disorders. New York: Human Press; 2010.
3. Taveira-Dasilva A M, Pacheco-Rodriguez G, Moss J. The natural history of lymphangioleiomyomatosis: markers of severity, rate of progression and prognosis. Lymphat Res Biol; 8(1):9-19.
4. Henske E P, McCormack F X. Lymphangioleiomyomatosis—a wolf in sheep's clothing. J Clin Invest 2012; 122(11):3807-3816.
5. Costello L C, Hartman T E, Ryu J H. High frequency of pulmonary lymphangioleiomyomatosis in women with tuberous sclerosis complex. Mayo Clin. Proc. 2000; 75(6):591-594.
6. Dabora S L, Jozwiak S, Franz D N, Roberts P S, Nieto A, Chung J, Choy Y S, Reeve M P, Thiele E, Egelhoff J C, Kasprzyk-Obara J, Domanska-Pakiela D, Kwiatkowski D J. Mutational analysis in a cohort of 224 tuberous sclerosis patients indicates increased severity of TSC2, compared with TSC1, disease in multiple organs. Am. J. Hum. Genet. 2001; 68(1):64-80.
7. Astrinidis A, Khare L, Carsillo T, Smolarek T, Au K S, Northrup H, Henske E P. Mutational analysis of the tuberous sclerosis gene TSC2 in patients with pulmonary lymphangioleiomyomatosis. J Med Genet 2000; 37(1): 55-57.
8. Strizheva G D, Carsillo T, Kruger W D, Sullivan E J, Ryu J H, Henske E P. The spectrum of mutations in TSC1 and TSC2 in women with tuberous sclerosis and lymphangiomyomatosis. Am J Respir Crit Care Med 2001; 163(1): 253-258.
9. Karbowniczek M, Astrinidis A, Balsara B R, Testa J R, Lium J H, Colby T V, McCormack F X, Henske E P. Recurrent lymphangiomyomatosis after transplantation: genetic analyses reveal a metastatic mechanism. Am J Respir Crit Care Med 2003; 167(7):976-982.
10. Bittmann I, Dose T B, Muller C, Dienemann H, Vogelmeier C, Lohrs U. Lymphangioleiomyomatosis: recurrence after single lung transplantation. Hum Pathol 1997; 28(12):1420-1423.
11. Sato N, Koinuma J, Ito T, Tsuchiya E, Kondo S, Nakamura Y, Daigo Y. Activation of an oncogenic TBC1D7 (TBC1 domain family, member 7) protein in pulmonary carcinogenesis. Genes Chromosomes Cancer 2010; 49(4):353-367.
12. Menon S, Dibble C C, Talbott G, Hoxhaj G, Valvezan A J, Takahashi H, Cantley L C, Manning B D. Spatial control of the TSC complex integrates insulin and nutrient regulation of mTORC1 at the lysosome. Cell 2014; 156 (4):771-785.
13. Dibble C C, Elis W, Menon S, Qin W, Klekota J, Asara J M, Finan P M, Kwiatkowski D J, Murphy L O, Manning B D. TBC1D7 is a third subunit of the TSC1-TSC2 complex upstream of mTORC1. Mol Cell 2012; 47(4): 535-546.
14. McCormack F X, Travis W D, Colby T V, Henske E P, Moss J. Lymphangioleiomyomatosis: calling it what it is: a low-grade, destructive, metastasizing neoplasm. Am J Respir Crit Care Med 2012; 186(12):1210-1212.
15. Moss J. Focus on Lymphangioleiomyomatosis. Introduction. Lymphat Res Biol 2010; 8(1):3.
16. Yu J, Henske E P. mTOR activation, lymphangiogenesis, and estrogen-mediated cell survival: the "perfect storm" of pro-metastatic factors in LAM pathogenesis. Lymphat Res Biol 2010; 8(1):43-49.
17. Goncharova E A, Goncharov D A, Eszterhas A, Hunter D S, Glassberg M K, Yeung R S, Walker C L, Noonan D, Kwiatkowski D J, Chou M M, Panettieri R A, Jr., Krymskaya V P. Tuberin regulates p70 S6 kinase activation and ribosomal protein S6 phosphorylation. A role for the TSC2 tumor suppressor gene in pulmonary lymphangioleiomyomatosis (LAM). J Biol Chem 2002; 277(34): 30958-30967.
18. Lee P S, Tsang S W, Moses M A, Trayes-Gibson Z, Hsiao L L, Jensen R, Squillace R, Kwiatkowski D J. Rapamycin-insensitive up-regulation of MMP2 and other genes in tuberous sclerosis complex 2-deficient lymphangioleiomyomatosis-like cells. Am J Respir Cell Mol Biol 2010; 42(2):227-234.

19. Krishnakumar R, Kraus W L. The PARP side of the nucleus: molecular actions, physiological outcomes, and clinical targets. Mol Cell 2010; 39(1):8-24.
20. Rouleau M, Patel A, Hendzel M J, Kaufmann S H, Poirier G G. PARP inhibition: PARP1 and beyond. Nat Rev Cancer 2010; 10(4):293-301.
21. Bryant H E, Schultz N, Thomas H D, Parker K M, Flower D, Lopez E, Kyle S, Meuth M, Curtin N J, Helleday T. Specific killing of BRCA2-deficient tumours with inhibitors of poly(ADP-ribose) polymerase. Nature 2005; 434(7035):913-917.
22. Farmer H, McCabe N, Lord C J, Tutt A N, Johnson D A, Richardson T B, Santarosa M, Dillon K J, Hickson I, Knights C, Martin N M, Jackson S P, Smith G C, Ashworth A. Targeting the DNA repair defect in BRCA mutant cells as a therapeutic strategy. Nature 2005; 434 (7035):917-921.
23. Chatterjee P, Choudhary G S, Sharma A, Singh K, Heston W D, Ciezki J, Klein E A, Almasan A. PARP inhibition sensitizes to low dose-rate radiation TMPRSS2-ERG fusion gene-expressing and PTEN-deficient prostate cancer cells. PLoS One 2013; 8(4):e60408.
24. Mendes-Pereira A M, Martin S A, Brough R, McCarthy A, Taylor J R, Kim J S, Waldman T, Lord C J, Ashworth A. Synthetic lethal targeting of PTEN mutant cells with PARP inhibitors. EMBO Mol Med 2009; 1(6-7):315-322.
25. Landi M T, Dracheva T, Rotunno M, Figueroa J D, Liu H, Dasgupta A, Mann F E, Fukuoka J, Hames M, Bergen A W, Murphy S E, Yang P, Pesatori A C, Consonni D, Bertazzi P A, Wacholder S, Shih J H, Caporaso N E, Jen J. Gene expression signature of cigarette smoking and its role in lung adenocarcinoma development and survival. PLoS One 2008; 3(2):e1651.
26. Lu T P, Tsai M H, Lee J M, Hsu C P, Chen P C, Lin C W, Shih J Y, Yang P C, Hsiao C K, Lai L C, Chuang E Y. Identification of a novel biomarker, SEMA5A, for non-small cell lung carcinoma in nonsmoking women. Cancer Epidemiol Biomarkers Prev 2010; 19(10):2590-2597.
27. Pacheco-Rodriguez G, Kumaki F, Steagall W K, Zhang Y, Ikeda Y, Lin J P, Billings E M, Moss J. Chemokine-enhanced chemotaxis of lymphangioleiomyomatosis cells with mutations in the tumor suppressor TSC2 gene. J Immunol 2009; 182(3):1270-1277.
28. Zhang H, Cicchetti G, Onda H, Koon H B, Asrican K, Bajraszewski N, Vazquez F, Carpenter C L, Kwiatkowski D J. Loss of Tsc1/Tsc2 activates mTOR and disrupts PI3K-Akt signaling through downregulation of PDGFR. J Clin Invest 2003; 112(8):1223-1233.
29. Pena-Llopis S, Vega-Rubin-de-Celis S, Schwartz J C, Wolff N C, Tran T A, Zou L, Xie X J, Corey D R, Brugarolas J. Regulation of TFEB and V-ATPases by mTORC1. EMBO J 2011; 30(16):3242-3258.
30. Duvel K, Yecies J L, Menon S, Raman P, Lipovsky A I, Souza A L, Triantafellow E, Ma Q, Gorski R, Cleaver S, Vander Heiden M G, MacKeigan J P, Finan P M, Clish C B, Murphy L O, Manning B D. Activation of a metabolic gene regulatory network downstream of mTOR complex 1. Mol Cell 2010; 39(2):171-183.
31. Yu J, Astrinidis A, Howard S, Henske E P. Estradiol and tamoxifen stimulate LAM-associated angiomyolipoma cell growth and activate both genomic and nongenomic signaling pathways. Am J Physiol Lung Cell Mol Physiol 2004; 286(4):L694-700.
32. Hong F, Larrea M D, Doughty C, Kwiatkowski D J, Squillace R, Slingerland J M. mTOR-raptor binds and activates SGK1 to regulate p27 phosphorylation. Mol Cell 2008; 30(6):701-711.
33. Howe S R, Gottardis M M, Everitt J I, Goldsworthy T L, Wolf D C, Walker C. Rodent model of reproductive tract leiomyomata. Establishment and characterization of tumor-derived cell lines. Am. J. Pathol. 1995; 146(6): 1568-1579.
34. Howe S R, Gottardis M M, Everitt J I, Walker C. Estrogen stimulation and tamoxifen inhibition of leiomyoma cell growth in vitro and in vivo. Endocrinology 1995; 136(11):4996-5003.
35. Astrinidis A, Cash T P, Hunter D S, Walker C L, Chernoff J, Henske E P. Tuberin, the tuberous sclerosis complex 2 tumor suppressor gene product, regulates Rho activation, cell adhesion and migration. Oncogene 2002; 21(55): 8470-8476.
36. Onda H, Lueck A, Marks P W, Warren H B, Kwiatkowski D J. Tsc2(+/−) mice develop tumors in multiple sites that express gelsolin and are influenced by genetic background. J Clin Invest 1999; 104(6):687-695.
37. Yu J J, Robb V A, Morrison T A, Ariazi E A, Karbowniczek M, Astrinidis A, Wang C, Hernandez-Cuebas L, Seeholzer L F, Nicolas E, Hensley H, Jordan V C, Walker C L, Henske E P. Estrogen promotes the survival and pulmonary metastasis of tuberin-null cells. Proc Natl Acad Sci USA 2009; 106(8):2635-2640.
38. Li C, Lee P S, Sun Y, Gu X, Zhang E, Guo Y, Wu C L, Auricchio N, Priolo C, Li J, Csibi A, Parkhitko A, Morrison T, Planaguma A, Kazani S, Israel E, Xu K F, Henske E P, Blenis J, Levy B D, Kwiatkowski D, Yu J J. Estradiol and mTORC2 cooperate to enhance prostaglandin biosynthesis and tumorigenesis in TSC2-deficient LAM cells. J Exp Med 2014; 211(1):15-28.
39. Finlay G A, Thannickal V J, Fanburg B L, Kwiatkowski D J. Platelet-derived growth factor-induced p42/44 mitogen-activated protein kinase activation and cellular growth is mediated by reactive oxygen species in the absence of TSC2/tuberin. Cancer Res 2005; 65(23): 10881-10890.
40. Dizdaroglu M. Oxidatively induced DNA damage: mechanisms, repair and disease. Cancer Lett 2012; 327 (1-2):26-47.
41. Storr S J, Woolston C M, Zhang Y, Martin S G. Redox environment, free radical, and oxidative DNA damage. Antioxid Redox Signal 2013; 18(18):2399-2408.
42. Sousa F G, Matuo R, Soares D G, Escargueil A E, Henriques J A, Larsen A K, Saffi J. PARPs and the DNA damage response. Carcinogenesis 2012; 33(8):1433-1440.
43. Javle M, Curtin N J. The role of PARP in DNA repair and its therapeutic exploitation. Br J Cancer 2011; 105(8): 1114-1122.
44. Costantino G, Macchiarulo A, Camaioni E, Pellicciari R. Modeling of poly(ADP-ribose)polymerase (PARP) inhibitors. Docking of ligands and quantitative structure-activity relationship analysis. J Med Chem 2001; 44(23): 3786-3794.
45. Eltze T, Boer R, Wagner T, Weinbrenner S, McDonald M C, Thiemermann C, Burkle A, Klein T. Imidazoquinolinone, imidazopyridine, and isoquinolindione derivatives as novel and potent inhibitors of the poly(ADP-ribose) polymerase (PARP): a comparison with standard PARP inhibitors. Mol Pharmacol 2008; 74(6):1587-1598.
46. Boulton S, Pemberton L C, Porteous J K, Curtin N J, Griffin R J, Golding B T, Durkacz B W. Potentiation of temozolomide-induced cytotoxicity: a comparative study of the biological effects of poly(ADP-ribose) polymerase inhibitors. Br J Cancer 1995; 72(4):849-856.

47. Bowman K J, White A, Golding B T, Griffin R J, Curtin N J. Potentiation of anti-cancer agent cytotoxicity by the potent poly(ADP-ribose) polymerase inhibitors N1J1025 and NU1064. Br J Cancer 1998; 78(10):1269-1277.
48. Menear K A, Adcock C, Boulter R, Cockcroft X L, Copsey L, Cranston A, Dillon K J, Drzewiecki J, Garman S, Gomez S, Javaid H, Kerrigan F, Knights C, Lau A, Loh V M, Jr., Matthews I T, Moore S, O'Connor M J, Smith G C, Martin N M. 4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1. J Med Chem 2008; 51(20):6581-6591.
49. Davies S P, Reddy H, Caivano M, Cohen P. Specificity and mechanism of action of some commonly used protein kinase inhibitors. Biochem J 2000; 351(Pt 1):95-105.
50. Feldman M E, Apsel B, Uotila A, Loewith R, Knight Z A, Ruggero D, Shokat K M, Active-site inhibitors of mTOR target rapamycin-resistant outputs of mTORC1 and mTORC2. PLoS Biol 2009; 7(2):e38.
51. Carracedo A, Ma L, Teruya-Feldstein J, Rojo F, Salmena L, Alimonti A, Egia A, Sasaki A T, Thomas G, Kozma S C, Papa A, Nardella C, Cantley L C, Baselga J, Pandolfi P P. Inhibition of mTORC1 leads to MAPK pathway activation through a PI3K-dependent feedback loop in human cancer. J Clin Invest 2008; 118(9):3065-3074.
52. Sabatini D M. mTOR and cancer: insights into a complex relationship. Nat Rev Cancer 2006; 6(9):729-734.
53. Zhou Z R, Zhu X D, Zhao W, Qu S, Su F, Huang S T, Ma J L, Li X Y. Poly(ADP-ribose) polymerase-1 regulates the mechanism of irradiation-induced CNE-2 human nasopharyngeal carcinoma cell autophagy and inhibition of autophagy contributes to the radiation sensitization of CNE-2 cells. Oncol Rep 2013; 29(6):2498-2506.
54. Boesten D M, de Vos-Houben J M, Timmermans L, den Hartog G J, Bast A, Hageman G J. Accelerated aging during chronic oxidative stress: a role for PARP-1. Oxid Med Cell Longev 2013; 2013:680414.
55. Garber K. PARP inhibitors bounce back. Nat Rev Drug Discov 2013; 12(10):725-727.
56. Karbowniczek M, Cash T, Cheung M, Robertson G P, Astrinidis A, Henske E P. Regulation of B-Raf kinase activity by tuberin and Rheb is mammalian target of rapamycin (mTOR)-independent. J Biol Chem 2004; 279 (29):29930-29937.
57. Karbowniczek M, Robertson G P, Henske E P. Rheb inhibits C-raf activity and B-raf/C-raf heterodimerization. J Biol Chem 2006; 281(35):25447-25456.
58. McCormack F X, Inoue Y, Moss J, Singer L G, Strange C, Nakata K, Barker A F, Chapman J T, Brantly M L, Stocks J M, Brown K K, Lynch J P, 3rd, Goldberg H J, Young L R, Kinder B W, Downey G P, Sullivan E J, Colby T V, McKay R T, Cohen M M, Korbee L, Taveira-DaSilva A M, Lee H S, Krischer J P, Trapnell B C, National Institutes of Health Rare Lung Diseases C, Group M T. Efficacy and safety of sirolimus in lymphangioleiomyomatosis. N Engl J Med 2011; 364(17):1595-1606.
59. Goncharova E A, Goncharov D A, Li H, Pimtong W, Lu S, Khavin I, Krymskaya V P. mTORC2 is Required for Proliferation and Survival of TSC2-Null Cells. Mol Cell Biol.
60. Parkhitko A, Myachina F, Morrison T A, Hindi K M, Auricchio N, Karbowniczek M, Wu J J, Finkel T, Kwiatkowski D J, Yu J J, Henske E P. Tumorigenesis in tuberous sclerosis complex is autophagy and p62/sequestosome 1 (SQSTM1)-dependent. Proc Natl Acad Sci USA 2011; 108(30):12455-12460.
61. Parkhitko A A, Priolo C, Coloff J L, Yun J, Wu J J, Mizumura K, Xu W, Malinowska I A, Yu J, Kwiatkowski D J, Locasale J W, Asara J M, Choi A M, Finkel T, Henske E P. Autophagy-dependent metabolic reprogramming sensitizes TSC2-deficient cells to the antimetabolite 6-aminonicotinamide. Mol Cancer Res 2014; 12(1):48-57.
62. Chang W Y, Clements D, Johnson S R. Effect of doxycycline on proliferation, MMP production, and adhesion in LAM-related cells. Am J Physiol Lung Cell Mol Physiol; 299(3):L393-400.

What is claimed is:

1. A method of treating a condition associated with mTORC1 hyperactivation selected from tuberous sclerosis complex (TSC) and lymphangioleiomyomatosis (LAM), the method comprising administering to a subject having the condition a pharmaceutically-effective amount of a poly (ADP-ribose) polymerase 1 (PARP1) inhibitor.

2. The method of claim 1, wherein the PARP inhibitor is selected from a small molecule, a nucleic acid, a nucleic acid analog or derivative at least long enough to target a PARP1 mRNA for cleavage or binding that inhibits PARP1 protein synthesis, or combinations thereof.

3. The method of claim 1, wherein the PARP1 inhibitor is selected from the group consisting of 8-hydroxy-2-methylquinazoline-4-one, 3,4-dihydro-5[4-(1-piperindinyl)butoxy]-1(2H)-isoquinoline, 3-aminobenzamide, olaparib, iniparib, rucaparib, veliparib, talazoparib, niraparib, CEP-9722, BGB-290, AG-14361, A966492 and BMN673.

4. The method of claim 2, wherein the PARP1 inhibitor is a small interfering RNA (siRNA).

5. The method of claim 1, wherein the subject is a mammal.

6. The method of claim 5, wherein the subject is a human.

7. The method of claim 1, wherein the administering is systemic.

8. The method of claim 1, wherein the administering is local.

* * * * *

SEQUENCE LISTING

<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccaagccagt tcaggacctc at                                              22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggatctgcct tttgctcagc ttc                                             23

<210> SEQ ID NO 3
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catggcgctt acctgatgag tc                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacagtgccc aggatgctga gt                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcctatggca aaggcatcta cc                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tctctggacc agctcatcct tg                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accgtatgtg aacgggagct gt                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccaacgcag acctacacat gg                                              22

<210> SEQ ID NO 9
<211> LENGTH: 22
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 9
ggcaaagagg tccaagatgc tg    22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gcctcacaca tctcttccac gt    22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gaatctcacc actggaaagc agc    23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
cattctccca gtgtggtggc at    22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctctgtcacc aaacctccac ac    22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gctactgctg acagtggtca ca    22

<210> SEQ ID NO 15
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 15
gcatttcatg gtagccgcct ag                                                  22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caagtcactg gtgaggtagg tc                                                  22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gattctcagg agcacttgga aag                                                 23

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggtgtggac agccttcgta gt                                                  22

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaggagatga ctccttcaac acc                                                 23

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgatgagctg ctcagggtgg aa                                                  22

<210> SEQ ID NO 21
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 21
ccatcggtgc aaatttaca                                                19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cattcgcatt cagtccata                                                19
```